(12) United States Patent
Pereira et al.

(10) Patent No.: US 7,091,243 B2
(45) Date of Patent: Aug. 15, 2006

(54) ANTI-IRRITANTS

(75) Inventors: Abel Pereira, Belleville, NJ (US);
Laurie Joseph, Cranbury, NJ (US);
Robert Comber, New City, NY (US)

(73) Assignee: Croda, Inc., Parsippany, NJ (US)

( * ) Notice: Subject to any disclaimer, the term of this patent is extended or adjusted under 35 U.S.C. 154(b) by 237 days.

(21) Appl. No.: 10/215,832

(22) Filed: Aug. 9, 2002

(65) Prior Publication Data

US 2003/0114520 A1   Jun. 19, 2003

Related U.S. Application Data

(60) Provisional application No. 60/316,608, filed on Aug. 31, 2001, provisional application No. 60/311,010, filed on Aug. 9, 2001.

(51) Int. Cl.
*A61K 31/235*   (2006.01)
*A61K 31/225*   (2006.01)
*C07C 69/76*   (2006.01)
*C07C 69/34*   (2006.01)

(52) U.S. Cl. .................. 514/532; 514/547; 560/89; 560/198

(58) Field of Classification Search .................. 424/59, 424/60, 66, 67, 68; 560/182, 190, 198, 204, 560/89; 514/785, 547, 532
See application file for complete search history.

(56) References Cited

U.S. PATENT DOCUMENTS

| | | | |
|---|---|---|---|
| 1,985,424 A | 12/1934 | Piggott | |
| 2,438,091 A | 3/1948 | Lynch | |
| 2,528,378 A | 10/1950 | Mannheimer | |
| 2,658,072 A | 11/1953 | Kosmin | |
| 2,703,798 A | 3/1955 | Schwartz | |
| 2,965,576 A | 12/1960 | Wilson | |
| 3,155,591 A | 11/1964 | Hilfer | |
| 3,755,560 A | 8/1973 | Dickert | |
| 3,929,678 A | 12/1975 | Laughlin et al. | |
| 3,959,461 A | 5/1976 | Bailey et al. | |
| 4,185,017 A | 1/1980 | Piesch et al. | |
| 4,261,851 A * | 4/1981 | Duke | 510/422 |
| 4,275,055 A | 6/1981 | Nachtigal et al. | |
| 4,387,090 A | 6/1983 | Bolich, Jr. | |
| 4,421,769 A | 12/1983 | Dixon et al. | |
| 4,557,853 A | 12/1985 | Collins | |
| 4,704,272 A | 11/1987 | Oh et al. | |
| 4,741,855 A | 5/1988 | Grote et al. | |
| 4,788,006 A | 11/1988 | Bolich, Jr. et al. | |
| 4,902,499 A | 2/1990 | Bolish, Jr. et al. | |
| 4,919,934 A | 4/1990 | Deckner et al. | |
| 4,976,953 A | 12/1990 | Orr et al. | |
| 5,011,681 A | 4/1991 | Ciotti et al. | |
| 5,120,532 A | 6/1992 | Wells et al. | |
| 5,151,209 A | 9/1992 | McCall et al. | |
| 5,151,210 A | 9/1992 | Steuri et al. | |
| 5,302,077 A | 4/1994 | Sato | |
| 5,382,377 A | 1/1995 | Raehse et al. | |
| 5,455,025 A * | 10/1995 | Pereira et al. | 424/59 |
| 5,597,555 A | 1/1997 | Pereira et al. | |
| 5,693,316 A | 12/1997 | Pereira | |
| 5,876,737 A | 3/1999 | Schönrock et al. | |
| 5,961,966 A | 10/1999 | Abend | |
| 6,312,714 B1 | 11/2001 | Prosise et al. | |
| 6,379,716 B1 | 4/2002 | Santhanam et al. | |
| 6,476,254 B1 * | 11/2002 | Pereira et al. | 560/198 |

FOREIGN PATENT DOCUMENTS

EP   095238 A2   11/1983

* cited by examiner

*Primary Examiner*—Taylor Victor Oh
(74) *Attorney, Agent, or Firm*—Lerner, David, Littenberg, Krumholz & Mentlik, LLP

(57) ABSTRACT

Alkoxylated esters of dicarboxylic or tricarboxylic acids have an anti-irritating activity measured as a reduction in intracellular leakage of sodium fluorescein of 15% or more at 1:50 dilution or 40% or more at 1:100 dilution from a test composition containing 5% of the alkoxylated ester. These alkoxylated esters are useful in cosmetic and personal care products, especially in products such as baby shampoos, hand dishwashing liquids and bubble bath preparations. A method of reducing irritation provides for application of an irritant with the alkoxylated esters to the subject in a personal care or cosmetic product.

72 Claims, No Drawings

ANTI-IRRITANTS

CROSS-REFERENCE TO RELATED APPLICATIONS

This patent application claims the benefit of the filing date of the U.S. Provisional Application No. 60/316,608, filed Aug. 31, 2001, and the U.S. Provisional Application No. 60/311,010, filed Aug. 9, 2001, the disclosures of which are hereby incorporated by reference.

FIELD OF THE INVENTION

The invention relates to the field of cosmetic and/or personal care products. More specifically, the invention relates to chemical compounds useful as anti-irritants in cosmetic and/or personal care products and methods of related methods of reducing irritation.

BACKGROUND OF THE INVENTION

Formulation and production of personal care products, such as shampoos, conditioners, depilatories, sunscreens and the like, presents a number of challenges. Some ingredients used in such products may contribute to skin and eye irritation. For example, shampoos usually include various surface-active compounds or surfactants, depilatories are formulated with organic or inorganic bases, and certain skin care preparations contain hydroxy acids, all of which may cause irritation. Additionally, certain products (e.g., soaps, detergents, cleansers, shaving creams, etc.) may remove some of the skin's protective lipids and thus increase skin's sensitivity to other formulation components, which might otherwise not produce irritation.

Whatever the cause of the irritation, many attempts have been made to reduce the irritation potential of personal care and cosmetic products by identifying ingredients that cause irritation, and reducing the concentration(s) of such ingredients or eliminating them entirely. However, in many cases, it may not be practical or desirable to reduce or eliminate the irritating ingredient, which is often the active ingredient of the formulation. For example, surfactants, bases, and hydroxy acids are included in shampoos, depilatories, and certain skin care products, respectively, to achieve the primary purpose of the product formulation. Therefore, instead of removing the irritants, it may be desirable to include anti-irritating compounds in the cosmetic and personal care formulations.

The use of anti-irritants in cosmetics had been suggested, for example, in articles by R. L. Goldemberg, Use of Anti-Irritants in Cosmetic Formulating, *J. Soc. Cosmetic Chemists*, 6: 317–340 (1965), and Anti-irritants, *J. Soc. Cosmetic Chemists*, 30:415–427 (1979), which are incorporated herein by reference. Goldemberg defined an anti-irritant as any agent "which when used in conjunction with skin or eye irritants, reduces their irritation sufficiently to be tolerated when applied to the body." A broader definition would consider a compound anti-irritating if it reduces irritation of the human body to any degree when used in combination with an irritant relative to the use of the same irritant, under the same conditions, without the anti-irritant.

In other words, a compound is generally considered anti-irritating if it reduces irritation when applied in a formulation with an irritant. Under this definition, any material that is applied separately from the irritating components of a product, e.g., before the product is applied, is generally not considered an anti-irritant. For example, there exists a known practice of applying a layer of petrolatum to the scalp before using a high-pH relaxer. Even though petrolatum does reduce scalp irritation by the relaxer, it would not be an anti-irritant because it is applied separately, unless petrolatum also reduces irritation when applied in a formulation with the relaxer.

Several mechanisms of anti-irritation activity had been suggested. One proposed mechanism involves a reduction in the irritating ability of the irritant by a complexation of the irritant with the anti-irritating compound. Polyvinyl pyrrolidone (PVP), which is known to reduce the irritating ability of iodine, is an example of anti-irritants that are believed to operate via this mechanism. When PVP is added to a solution of iodine, the latter no longer irritates mucousal tissue while retaining its germicidal activity.

Another suggested mechanism is blocking of chemically reactive sites of skin keratin by the anti-irritant, which thus prevents the irritant from accessing the reactive sites. For example, polyquaternium-10 and stearyl dimethylamine oxide are thought to operate by this mechanism.

Yet another suggested mechanism is a reduction in the degree of physical contact between the irritant and the skin. Good examples of raw materials that operate via this mechanism are thickeners that retard the rate at which irritants are be replenished at the skin/formulation interface.

Several methods have been used in measuring the irritation values. The examples of in vivo methods of measuring irritation and anti-irritating effects include Repeated Insult Patch Testing (RIPT) and Draize methods, both known to those skilled in the art. The examples of in vitro methods are Eyetex™ by InVitro International, and EpiDerm™ and EpiOcular™ by MatTek Corporation. Another method of measuring irritation was described by R. Goldemberg in Reduction of Topical Irritation, *J. Soc. Cosmetic Chemists*, 28, 667–679 (1977), which is incorporated by reference herein.

The art of reducing irritation has not been perfected and the need still exists for effective anti-irritants. For example, there exists a need for ingredients that reduce the irritation produced by surfactant-based cosmetic and/or personal care formulations. Anti-irritants which are easily compatible with the personal care formulations and/or which are able to contribute other advantageous properties such as such as stabilization, wetability, spreadability, viscosity, etc., are particularly desirable. It is especially desirable to find anti-irritants that are also able to contribute to a superior afterfeel of the product and/or allow the formulation of a clear product.

SUMMARY OF THE INVENTION

The present invention addresses these needs by providing, in one of the preferred aspects, alkoxylated esters of dicarboxylic or tricarboxylic acid having defined anti-irritation activity measured as a reduction in the degree of irritation realized by applying the same formulation, with or without the anti-irritating compounds of the invention, to the same skin surface for the same time, and comparing the results. Anti-irritation properties can also be measured by showing a reduction in the intracellular leakage of sodium fluorescein in the test composition in reference to a control composition. The preferred alkoxylated esters have anti-irritation activity of 15% or more at 1:50 dilution or 40% or more at 1:100 dilution from a test composition containing 5% by weight of the alkoxylated ester. Another preferred aspect of the present invention, provides alkoxylated esters having defined chemical structures. More preferably, the alkoxylated esters of the specified chemical structures also exhibit anti-irritation activity.

In accordance with another preferred aspect, the invention provides a method of reducing irritation caused to a human or animal subject from the application of a personal care or cosmetic product containing an irritant. The method includes applying personal care or cosmetic products which includes both an irritant and at least one alkoxylated ester of dicarboxylic or tricarboxylic acid, which has defined anti-irritating activity. The method of the invention is especially useful for reducing irritation from surfactants typically found in personal care or cosmetic products.

In accordance with yet another preferred aspect, the invention provides compositions including an irritant, which is preferably a surfactant, and at least one alkoxylated ester described herein. Preferably, the alkoxylated esters of the composition have defined the anti-irritation activity. Preferably, the compositions may be provided as dilutable, pre-mixed blends or as product formulations. Various additional ingredients may be included in the compositions. The invention is further described in reference to the preferred embodiments.

DETAILED DESCRIPTION OF PREFERRED EMBODIMENTS

It has been surprisingly discovered that some alkoxylated esters reduce irritation potential of a composition containing an irritant when present in the composition along with the irritant and thus exhibit anti-irritation activity. Alkoxylated esters of dicarboxylic acid are monoesters or diesters of alkoxylated alcohols and dicarboxylic acid. Alkoxylated esters of tricarboxylic acids are diesters or triesters of alkoxylated alcohols and tricarboxylic acids. Some of these esters are disclosed in U.S. Pat. Nos. 5,382,377, 5,455,025 and 5,597,555, and U.S. patent application Ser. No. 09/410, 585, all of which are incorporated herein by reference in their entirety, and are assigned to Croda Incorporated of Piscataway, N.J., the assignee of the present patent application. These compounds are disclosed as excellent emollients. Others are disclosed herein.

The following example illustrates the discovery of the anti-irritation activity of certain alkoxylated esters. A test composition A and a control composition B were prepared. The test composition A contained 5% of Di-PPG-3-PEG-4 Myristyl Ether Adipate, an alkoxylated (tripropoxy-tetraethoxy) diester of tripropoxy-tetraethoxy myristyl alcohol and adipic acid, and 10% of sodium laurel sulfate (SLS), a known irritant, in Phosphate Buffered Saline (PBS) at pH 6.8–7.2. The control composition B contained 10% SLS in PBS at the same pH without the alkoxylated ester. A separate solution of PBS (without SLS and the ester) was used as a negative control solution. The testing was carried out on Epiocular™, Tissue Model (OCL-200), from MatTek Corporation. Epiocular™ inserts were equilibrated overnight in assay media. Test composition A and B, and the negative control solution were then separately placed in direct contact with the cells. For each test substance, the progress of cell death was measured at 1, 5, and 10 minutes. The negative control inserts were exposed to phosphate buffered saline (PBS) for 10 minutes. The inserts were washed with PBS, equilibrated in Eagle's Minimal Essential Medium (EMEM) prior to incubation in MTT (3-[4,5-Dimethylthiazol-2-yl]-2,5-diphenyltetrazolium bromide), and extracted in isopropyl alcohol overnight. The optical density of the tested incubated samples was compared to the negative control insert PBS (100% viability).

TABLE 1 shows the percentages of cell survival for the test composition A and the control composition B:

TABLE 1

| | Cell survival (%) | |
|---|---|---|
| Time (min) | Composition A (SLS + Di-PPG-3-PEG-4 Myristyl Ether Adipate) | Composition B (SLS only) |
| 0 | 100 | 100 |
| 1 | 97.79 | 72.56 |
| 5 | 82.18 | 52.16 |
| 10 | 64.25 | 31.75 |

As seen from TABLE 1, the addition of Di-PPG-3-PEG-4 Myristyl Ether Adipate substantially reduces cell death and thus suggested that Di-PPG-3-PEG-4 Myristyl Ether Adipate possesses anti-irritation activity.

Not all alkoxylated esters of dicarboxylic or tricarboxylic acids possess the desired anti-irritating activity. In this regard, only alkoxylated esters having certain minimal anti-irritation activity may be suitable for practical use as anti-irritants (defined anti-irritating activity). Further, the alkoxylated esters having greater anti-irritation activity are preferred.

In accordance with the preferred embodiment of the invention, pre-defined criteria of anti-irritation activity are used to select preferred alkoxylated esters. The alkoxylated esters that meet such criteria are selected preferentially for formulating the personal care and cosmetic products containing irritants. The tested alkoxylated esters are evaluated based on measuring irritation potentials of a test composition(s), which contains an irritant and a candidate alkoxylated ester, and a control composition, which is essentially identical but lacks the candidate alkoxylated ester. The measured irritation potentials of the test composition(s) and the control composition are compared. The magnitude of reduction, if any, in the irritation potentials of the test composition(s) in reference to the control is the measure of anti-irritation activity of the candidate alkoxylated ester. The pre-defined criteria for selection are threshold(s) of reduction in the irritation potential. The candidates that have activity greater than the pre-determined criteria are selected. The pre-defined selection criteria are also used to separate the esters into classes in accordance with the magnitude of the anti-irritation activity.

The test methodology for measuring the irritation potential of alkoxylated esters is Trans-Epithelial Permeability (TEP) Assay. The TEP Assay measures intracellular leakage of a suitable marker reagent, such as sodium fluorescein, through cells that were exposed to irritant-containing compositions. Smaller leakage indicates lower degree of cell damage. If the cells are exposed to an irritant-containing composition with and without an anti-irritant, the magnitude of reduction in the intracellular leakage measures the anti-irritating ability of the anti-irritant. For additional discussion of the TEP Assay, see Tchao, R., Trans-Epithelial Permeability of Fluorescein In Vitro As An Assay To Determine Eye Irritants, Progress in In Vitro Toxicology, A M Goldberg ed., 6:271–283 (1988); Drewitt-Barlow, B., McPherson, J., Broyd, J. and Williamson, 2000. No Tears for Baby. Global Cosmetic Industry, (October, 2000): 16–20; Burke, J. and Joseph, L. B., 2000, In Vitro Analysis of the Irritation Mitigating Properties of PEG-150 Pentaerythrityl Tetrastearate, Society of Cosmetic Chemists, 2000 Technology Showcase, NY, N.Y., all of which are incorporated by reference herein.

The following example illustrates the test methodology for and selection of the alkoxylated esters. Test compositions I, II, and III, and control composition IV were prepared. Table 2 shows the content of the compositions I, II, III, and IV:

TABLE 2

| Component | I | II | III | IV |
|---|---|---|---|---|
| Cocamidopropyl Hydroxysultaine | 12% | 12% | 12% | 12% |
| SLES (3)* | 20% | 20% | 20% | 20% |
| Di-PPG-2-PEG-10 Lauryl Adipate** | 5% | — | — | — |
| Di-PPG-2 Myreth-10 Adipate*** | — | 5% | — | — |
| Bis-PPG-2 Steareth-10 Adipate**** | — | — | 5% | — |
| Water | qs | qs | qs | qs |

*Sodium laurel ether sulfate (tri-ethoxylated)
**di-ester of di-(propoxy)-deca-(ethoxy) laurel ($C_{12}$) alcohol and adipic acid;
***di-ester of di-(propoxy)-deca-(ethoxy) myristyl ($C_{14}$) alcohol and adipic acid;
****di-ester of di-(propoxy)-deca-(ethoxy) stearyl ($C_{18}$) alcohol and adipic acid.

The ingredients were dissolved in distilled water and pH was adjusted to 6.8 to 7.2. Sodium laurel ether sulfate (triethoxylated) is a known irritant. The irritation potentials of the compositions I, II, III and IV were measured using the TEP assay as follows.

MDCK (Kidney, Canine) strain NBL-2 purchased from American Type Culture Collection (CCL 34) were cultured under standard conditions. Three days prior to experimentation the cells were subcultured onto Corning 6.5 mm Transwell porous cell culture inserts at $1 \times 10^5$ cells per insert. Cells are grown to confluence in 3 days. The inserts were washed 5 times with phosphate buffered saline (PBS) immediately before testing. All reagents were made prior to experimentation, with the exception of the final dilutions with a saline solution, which were prepared on the day of the experiment.

The compositions I, II, III, and IV were diluted to 1:50 and 1:100 with Hanks Buffered Saline Solution (HBSS). For example, to prepare a 1:50 dilution of the test composition I, 1 part of the test composition I was mixed with 49 parts of HBSS. The diluted samples were placed on the ventral side of the insert (in duplicate) in direct contact with the cells for 15 minutes. Two inserts with HBSS were used as the negative control and inserts without cells were used as references of 100% leakage. After application of the test article, the inserts were washed with large amounts of PBS.

Sodium fluorescein was added directly to the cell monolayer and 1 ml of HBSS was placed in the well below. After 30 minutes of incubation at room temperature triplicate 200 μl samples were removed from the well and the optical density (OD) of the well fluid was determined. The experimental OD was then compared to the OD of 100% leakage reference (filter without cells), and provided a measure of irritation potential of the tested compositions.

Table 3 shows the percentages of the intracellular leakage of sodium fluorescein for cells exposed to the tests compositions I, II, III, and the control composition IV:

TABLE 3

| Compositions | Ester | Percentage Leakage (1:50 dilution) | Percentage Leakage (1:100 Dilution) |
|---|---|---|---|
| I | Di-PPG-2-PEG-10 Lauryl Adipate | 69% | 64% |
| II | Di-PPG-2-PEG-10 Myristyl Adipate | 65% | 43% |
| III | Di-PPG-2-PEG-10 Steareth Adipate | 44% | 27% |
| IV (control) | — | 73% | 68% |

As seen from Table 3, substantial reductions in the intracellular leakage, and thus in the irritation potential, were observed for test compositions, especially for test compositions II and III, in comparison with the control composition IV. The reductions in the irritation potential were calculated as the percentage of the absolute reduction relative to the control formulation (control is taken as 100%, and the percentages of reduction are calculated as 100% minus (observed leakage)/(observed leakage of control)× 100%). The results of the calculations are shown in Table 4:

TABLE 4

| Compositions | Ester | Reduction in irritation potential (1:50 dilution) | Reduction in irritation potential (1:50 dilution) |
|---|---|---|---|
| I | Di-PPG-2-PEG-10 Lauryl Adipate | 5.4%* | 5.8% |
| II | Di-PPG-2-PEG-10 Myristyl Adipate | 11% | 36.7% |
| III | Di-PPG-2-PEG-10 Steareth Adipate | 39.8% | 60.2% |
| IV (control) | — | 0% | 0% |

*e.g., $(100\% - (69/73) \times 100\% = 5.4\%)$.

As seen from Table 4, there are substantial differences in the anti-irritation activity of different alkoxylated esters, notwithstanding similarities in the chemical structures. Also, the test methodology described above allows differentiation between anti-irritation activities of alkoxylated esters and creation of selection criteria for preferred alkoxylated esters having desired anti-irritation activity.

Thus, in accordance with one preferred aspect, the invention provides alkoxylated esters of dicarboxylic or tricarboxylic acid possessing an anti-irritation activity, measured as a reduction in intracellular leakage of sodium fluorescein, of 15% or more, when measured at 1:50 dilution, or 40% or more, when measured at 1:100 dilution of the test composition, in comparison to the control composition. More preferred alkoxylated esters reduce intracellular leakage of sodium fluorescein by 20% or more, when measured at 1:50 dilution, or by 50% or more when measured at 1:100 dilution. Yet more preferred alkoxylated esters reduce intracellular leakage of sodium fluorescein by 50% or more, when measured at 1:50 dilution, or by 75% or more when measured at 1:100 dilution. The reductions in the intracellular leakage of sodium fluorescein are measured by a Trans-Epithelial Permeability (TEP) Assay as described, and is a measure of the anti-irritation activity. The test composition is a solution of 5% of the candidate alkoxylated ester, 12% of cocamidopropyl hydroxysultaine, and 20% of tri-ethoxylated sodium laurel ether sulfate in distilled water and the control composition is a solution of 12% of cocamidopropyl hydroxysultaine and 20% of tri-ethoxylated sodium laurel ether sulfate in distilled water without the candidate alkoxylated ester, all components by weight of the compositions.

The invention also provides certain alkoxylated esters of specific chemical structures. More preferably, the alkoxylated esters having the described chemical structures also meet the selection criteria of anti-irritation activity described above.

In one preferred embodiment, the alkoxylated esters have the formula (I):

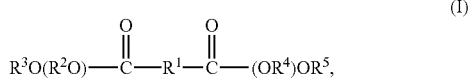

where —$COR^1CO$— is a dicarboxylic group of an aliphatic dicarboxylic acid, $R^1$ is an alkyl group, saturated or unsaturated, straight chain or branched, substituted or unsubstituted, cyclic or acyclic, having 0 to 20 carbon atoms, more preferably, 0 to 18 carbon atoms, yet more preferably, 0 to 8 carbon atoms, most preferably, 0 to 6 carbon atoms.

Alternatively, —$COR^1CO$— is a dicarboxylic group of an aromatic dicarboxylic acid, where $R^1$ is an aromatic nucleus of the aromatic dicarboxylic acid, having 6 to 20 carbon atoms, more preferably, 6 to 14 carbon atoms, yet more preferably, 6 or 10 carbon atoms. Non-limiting examples of the aromatic nucleus are aryl-, phenylaryl-, alkylaryl-, and naphthalene.

In the esters of the formula (I), $R^2O$— and $R^4O$—, which may be the same or different, are alkoxylated moieties of the formula

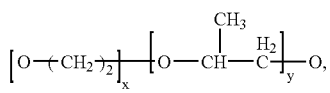

where [$O(CH_2)_2$—] is an ethoxy group and [$OCH(CH_3)CH_2$—] is a propoxy group, the alkoxylated moieties having any structural order of ethoxy and propoxy groups, which may thus be placed randomly, in blocks, or in alternating patterns;

x ranges from 0 to 200, preferably, 1 to 100, and y ranges from 0 to 200, preferably, 0 to 100;

$R^3$ and $R^5$, which may be the same or different, are independently hydrogen or alkyl, alkylaryl, or arylalkyl groups, straight chain or branched, saturated or unsaturated, substituted or unsubstituted, containing from 6 to 30 carbon atoms with the proviso that not more than one of $R^3$ and $R^5$ can be hydrogen.

Preferably, $R^3$ and $R^5$ have from 12 to 22 carbon atoms, more preferably, 16 to 22 carbon atoms, most preferably, 18 to 22 carbon atoms; x ranges from 1 to 40, yet more preferably, from 2 to 20, most preferably, x ranges from 3 to 10; y ranges from 0 to 40, more preferably, 1 to 10, most preferably, y ranges from 1 to 5; x/y ranges from 1 to 2.5, most preferably, from 1 to 2; the weight percentage of the ethoxy groups in the groups ($R^2O$) and ($R^4O$) with respect to the molecular weight of the groups $R^3O(R^2O)$— and $R^5O(R^4O)$—, respectively, is 20% or more, more preferably, from 20 to 80%, most preferably, from 24 to 35%.

In another preferred embodiment, the alkoxylated esters have formula (II):

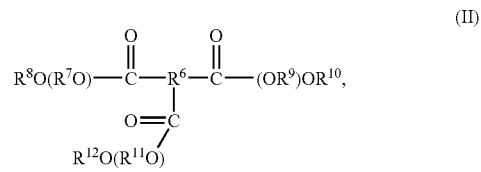

where —$COR^6CO$— is a tricarboxylic group of aliphatic tricarboxylic acid, and $R^6$ is an alkyl group, substituted or unsubstituted, saturated or unsaturated, straight chain or branched, cyclic or acyclic, having 1 to 19 carbon atoms, more preferably, 1 to 15 carbon atoms, yet more preferably, 1 to 8 carbon atoms, most preferably, 1 to 6 carbon atoms.

Alternatively, —$COR^6CO$— is a tricarboxylic group of aromatic tricarboxylic acid and $R^6$ is an aromatic nucleus of the aromatic tricarboxylic acid having 6 to 20 carbon atoms, more preferably, 6 to 14 carbon atoms, yet more preferably, 6 or 10 carbon atoms. Non-limiting examples of the $R^6$ nucleus are aryl-, phenylaryl-, alkylaryl-, and naphthalene.

In the esters of the formula (II), $R^7O$—, $R^9O$, and $R^{11}O$—, which may be same or different, are alkoxylated moieties of the formula

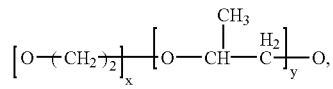

where [$O(CH_2)_2$—] is an ethoxy group and [$OCH(CH_3)CH_2$—] is a propoxy group, the alkoxylated moieties having any structural order of ethoxy and propoxy groups, which may thus be placed randomly, in blocks, or in alternating patterns;

x ranges from 0 to 200, preferably, from 1 to 100, and y ranges from 0 to 200, more preferably, from 0 to 100;

$R^8$, $R^{10}$, and $R^{12}$ are each independently alkyl, alkylaryl, or arylalkyl groups, straight chain or branched, saturated or unsaturated, substituted or unsubstituted, containing from 6 to 30 carbon atoms, or hydrogen, with the proviso that not more than one of $R^8$, $R^{10}$, and $R^{12}$ can be hydrogen.

Preferably, $R^8$, $R^{10}$, and $R^{12}$ have 12 to 22 carbon atoms, more preferably, 16 to 22 carbon atoms, most preferably, 18 to 22 carbon atoms; x ranges from 1 to 40, more preferably, from 2 to 20; y ranges from 0 to 40, more preferably, from 1 to 10; most preferably, x ranges from 3 to 10 and y ranges from 1 to 5, with x/y being 2 or greater and x>y; the weight percentage of the ethoxy groups in the groups (R$^7$O), (R$^9$O), and (R$^{11}$O) with respect to the molecular weight of the groups R$^8$O(R$^7$O)—, R$^{10}$O(R$^9$O)—, and R$^{12}$O(R$^{11}$O)—, respectively, is 20% or more, more preferably, from 20 to 80%, most preferably, from 24 to 35%.

It has also been found that alkoxylated esters having longer terminal alkyl chain have better anti-irritation activities. Referring to Table 4, Di-PPG-2-PEG-10 Steareth Adipate shows greater anti-irritating activity than Di-PPG-2-PEG-10 Myristyl Adipate, which, in turn, shows greater anti-irritating activity than Di-PPG-2-PEG-10 Lauryl Adipate. The anti-irritating activity substantially increases with the increase in the chain length.

In another preferred embodiment, the alkoxylated esters have the formula (III):

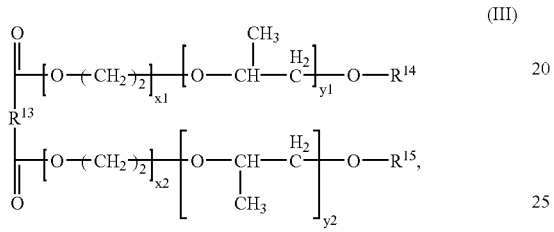

(III)

wherein —OCR$^{13}$CO— is a dicarboxylic group of aliphatic dicarboxylic acid, R$^{13}$ is a straight chain alkyl group, saturated or unsaturated, substituted or unsubstituted, cyclic or acyclic, having 0 to 20 carbon atoms, or —COR$^{13}$CO— is a dicarboxylic group of an aromatic dicarboxylic acid and R$^{13}$ is an aromatic nucleus of the aromatic dicarboxylic acid having 6 to 20 carbon atoms;

x1 and x2, which may be same or different, are ranging from 0 to 200, y1 and y2, which may be the same or different, are ranging from 0 to 200;

R$^{14}$ and R$^{15}$, may be the same or different, are alkyl groups, straight chain or branched, saturated or unsaturated, substituted or unsubstituted, having 16 to 30 carbon atoms, more preferably, 16 to 22 carbon atoms, most preferably, 18 to 22 carbon atoms.

Preferably, x1 and x2 are ranging from 0 to 100, more preferably, from 1 to 20; yet more preferably, from 2 to 10: y1 and y2 are ranging from 0 to 100, more preferably, from 1 to 10, yet more preferably, y1 and y2 range from 1 to 5; x1/y1 and x2/y2, same or different, are greater than 1; the group —OCR$^{13}$CO— has terminal carboxylic groups, R$^{13}$ has the structure (CH$_m$)$_n$ or —(CH$_m$)$_n$X, where X, if present, is a branch substituent in any position between the terminal carboxylic groups, and selected from the group consisting of lower alkyl, including methyl, hydroxy, alkylhydroxy, and halogen, including chloro and bromo, m is 1 or 2, and n is from 3 to 10, more preferably, from 3 to 7, most preferably, n is 4.

For a group of especially preferred esters of the formula (III), n is 4, R$^{14}$ and R$^{15}$ have 18 to 22 carbon atoms, x1 and x2 are 4, and y1 and y2 are 3. One of the particularly preferred esters of this group, in which R$^{14}$ and R$^{15}$ have 18 carbon atoms, may be referred to as di-PEG-4-PPG-3 steareth ether adipate. For another group of especially preferred esters of the formula (III), n is 4, R$^{14}$ and R$^{15}$ have 18 to 22 carbon atoms, x1 and x2 are 10, and y1 and y2 are 2. One of the particularly preferred esters of this group, in which R$^{14}$ and R$^{15}$ have 18 carbon atoms, may be referred to as di-PEG-2-PPG-10 steareth ether adipate.

Non-limiting examples of the alkoxylated esters of the formula (III) include

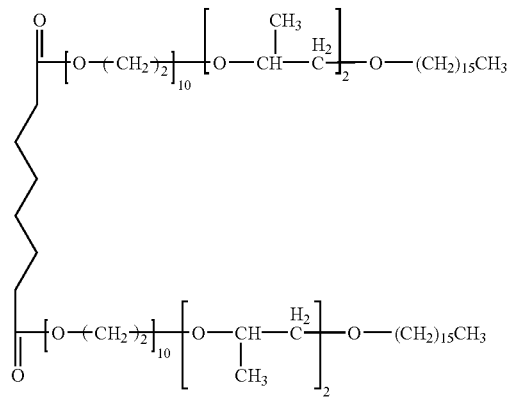

Di-PPG-2-PEG-10 Cetyl Ether Adipate

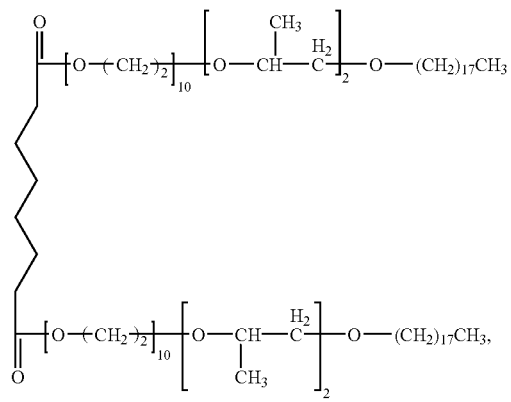

Di-PPG-2-PEG-10 Steareth Ether Adipate

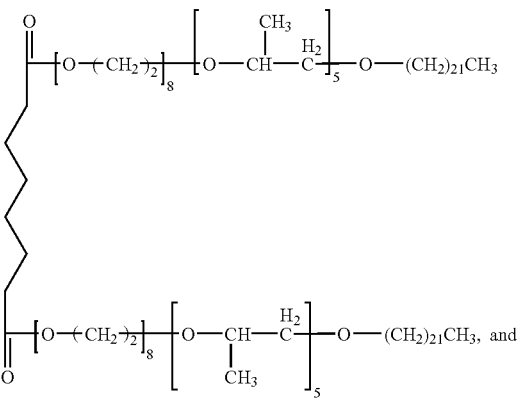

Di-PPG-5-PEG-8 Behenyl Ether Adipate

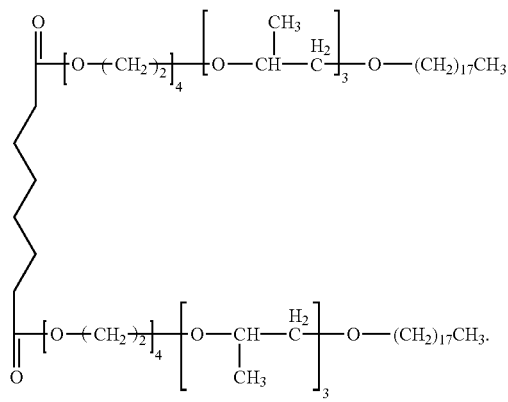

Di-PPG-3-PEG-4 Steareth Ether Adipate

It has also been found that alkoxylated esters that have certain patterns of alkoxylation show improved anti-irritation activity. In accordance with another preferred embodiment, the alkoxylated esters have the formula (IV):

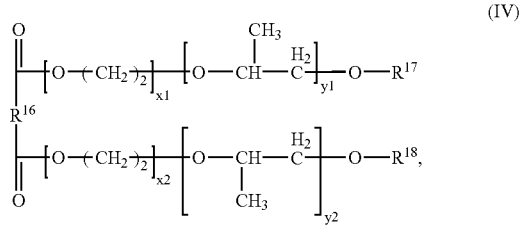

wherein —OCR$^{16}$CO— is a dicarboxylic group of aliphatic dicarboxylic acid and R$^{16}$ is an alkyl group, saturated or unsaturated, straight chain or branched, substituted or unsubstituted, cyclic or acyclic, having 0 to 20 carbon atoms;

R$^{17}$ and R$^{18}$ are alkyl groups, same or different, saturated or unsaturated, substituted or unsubstituted, having from 6 to 22 carbon atoms, more preferably, 12 to 22 carbon atoms, most preferably, 16 to 22 carbon atoms;

x1 and x2, which may be the same or different, range from 1 to 100, and y1 and y2, which may be the same or different, range from 0 to 100; and x1/y1 and x2/y2 vary from 1 to 2.5.

Preferably, x1/y1 and x2/y2 vary from 1 to 2, more preferably, from 1 to 1.5; x1 and x2 range from 1 to 40, more preferably, from 2 to 20, most preferably, from 3 to 10, y1 and y2 range from 0 to 40, more preferably, from 1 to 10, most preferably, from 1 to 5; R$^{16}$ is a group of the structure —(CH$_m$)$_n$ or —(CH$_m$)$_n$X, where m, n, and X are defined in reference to the formula (III).

For a group of especially preferred esters of the formula (IV), R$^{16}$ is the group of the structure —(CH$_2$)$_4$, R$^{17}$ and R$^{18}$ have 14 to 22 carbon atoms, x1 and x2 are 4, and y1 and y2 are 3. One of the particularly preferred esters of this group, in which R$^{17}$ and R$^{18}$ have 14 carbon atoms, may be referred to as di-PEG-4-PPG-3 myristyl ether adipate.

Non-limiting examples of the alkoxylated esters of the formula (IV) include

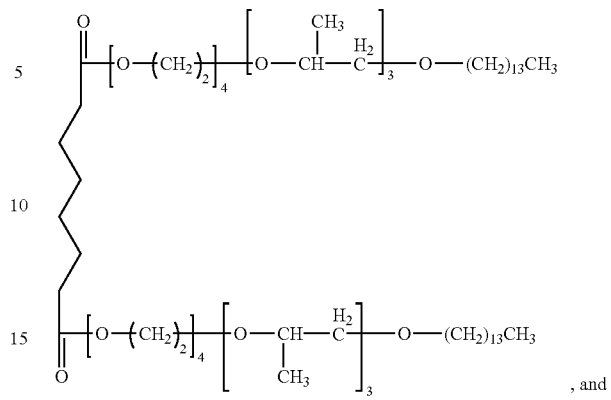

Di-PPG-3-PEG-4 Myristyl Ether Adipate

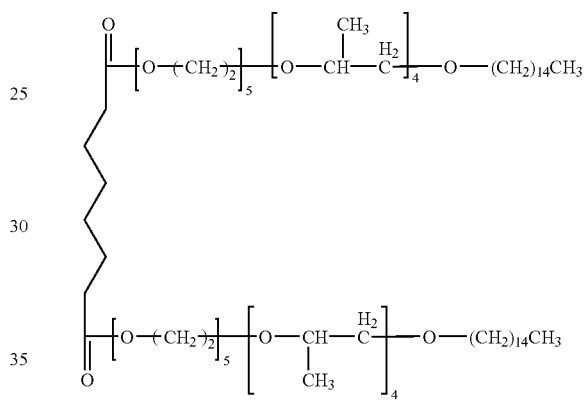

Di-PPG-4-PEG-5 Pentadecyl Ether Adipate

The compounds of the invention may be formed by reacting a corresponding di- or tricarboxylic acid with a desired alkoxylated fatty alcohol. Thus, in accordance with another aspect, the invention provides compounds formed by reacting the acid with a stoichiometric excess of one or more alkoxylated fatty alcohols.

In fact, the compounds of the invention may be produced in this manner by initially reacting, either sequentially, or in their mixed forms, saturated or unsaturated, substituted or unsubstituted, aliphatic or aromatic fatty alcohols, with an ethylene oxide, and/or propylene oxide, or mixtures thereof, in the presence of an acidic or basic catalyst. Catalysts suitable for this reaction are known in the art and include, for example, alkali metal oxides and hydroxides, e.g., potassium hydroxide, sodium methoxide, sodium borohydride, protic and Lewis acids, e.g., boron trifluoride, stannic chloride, and sulfuric acid. Amines, quaternary ammonium compounds, water and other acids may also be employed. Mixtures of catalysts may also be employed. Certain reactive substrates known in the art, for example, acetylenic alkanols, may eliminate the need for a catalyst. Inorganic catalysts such as tin catalysts may also be used.

Preferably, a basic catalyst is used in this reaction and, most preferably, from about 0.1 to about 2.0 weight percent of potassium or sodium hydroxide, sodium methoxide, sodium borohydride or mixtures thereof, based on the weight of the alcohol. The reaction is carried out under anhydrous conditions to avoid formation of by-products, and at a temperature which is, preferably, in the range of from about 110° C. to about 200° C., although higher temperatures may be utilized. The reaction can be carried out at a substantially atmospheric pressure, although it is preferably carried out in an autoclave at pressures of from about 10 psig to about 80 psig. Ethylene oxide and/or propylene oxide may also be added as a mixture or in any desired sequence, including alternate addition and sequential addition. The amount of ethylene oxide or propylene oxide introduced to the reaction zone, and the duration of reaction time, determines the number of moles of such components added to the fatty moiety, R, of the fatty alcohol.

Stoichiometric quantities of fatty alcohols, ethylene oxide and propylene oxide may be reacted together, and stoichiometric quantities of the polyalkoxylated fatty alcohol and dicarboxylic acid may be reacted together. The reaction, may, for example, be carried out sequentially in that the fatty alcohol is first reacted with the propylene oxide and, after the completion of the reaction, ethylene oxide is introduced into the reaction mixture, or vice versa.

The resulting polyalkoxylated fatty alcohol is then reacted with a suitable di or tricarboxylic acid. Examples of suitable aliphatic dicarboxylic acids include adipic acid, sebacic acid, malonic acid, and succinic acid. Adipic acid is preferred. Specific examples of suitable aromatic dicarboxylic acids are phthalic acid and naphthalene dicarboxylic acid.

The reaction between the alcohol and the acid is a conventional esterification reaction. The reaction may be carried out with or without a catalyst. The preferred catalysts include methane sulfonic acid and paratoluene sulfonic acid. The esterification is typically performed by combining stoichiometric quantities of the polyalkoxylated fatty alcohol and the acid to be esterified. As understood by those of ordinary skill in the art, when two polyalkoxylated fatty alcohol chains are to be added to the acid, the polyalkoxylated fatty alcohol and acid to be esterified are combined in a molar ratio of 2:1. However, slight stoichiometric excess may be employed to insure complete esterification and a low acidity. The esterification reaction may be carried out with or without a solvent.

Generally, the polyalkoxylated fatty alcohol, acid and catalyst are combined with mixing to form a reaction mixture. The reaction mixture is heated with mixing at a temperature between about 155° C. and about 250° C., and preferably at a temperature between about 170° C. and 220° C. until an acid value of less than 8 mg KOH, and preferably less than 5 mg KOH is obtained. The reaction mixture is then cooled below 85° C. and washed with water, preferably without neutralizing the catalyst. Higher temperatures should be avoided to prevent loss of the polyalkoxylated fatty alcohols and, consequently, incomplete esterification and higher than desired acidity. The ester layer is separated and heated under vacuum until moisture content of less than 0.2 percent is obtained.

As noted above, the polyalkoxylated fatty alcohols can be prepared by reacting mixed forms of fatty alcohols with mixtures of ethylene oxide and propylene oxide. Therefore, the resulting polyalkoxylated fatty alcohol can contain a mixture derived from the ethoxylation and the propoxylation of mixtures of fatty alcohols.

In accordance with another preferred aspect, the invention provides a method of reducing irritation from irritants, such as surfactants, hydroxy acids and others, present in a personal care or cosmetic product. U.S. Pat. Nos. 6,312,714, 6,379,716, and 5,876,737 describe certain types of irritants and compositions containing the irritants, and are incorporated herein by reference. Under the method of this aspect of the invention, the personal care or cosmetic product is formulated to contain the irritant(s) and at least one alkoxylated ester of dicarboxylic or tricarboxylic acid, having defined anti-irritating properties and then applied to a human or animal subject. The product may be applied to the body of the subject, including the subject's hair, skin and eyes, in a manner usual for the given product formulation. For example, a shampoo or conditioner formulation is applied to the hair and then rinsed; the skin care product is topically applied to the skin; and so on. Preferably, the alkoxylated esters are used to reduce irritation from surfactants.

The alkoxylated esters having anti-irritation activity, measured as a reduction in intracellular leakage of sodium fluorescein, of 15% or more at 1:50 dilution, or 40% or more at 1:100 dilution are preferred for practicing the method of the invention. More preferred are alkoxylated esters having anti-irritation activity of 20% or more at 1:50 dilution or 50% or more at 1:100 dilution, yet more preferred alkoxylated esters have anti-irritation activity of 40% or more at 1:50 dilution or 75% or more at 1:100 dilution. While alkoxylated esters having anti-irritation activity of less than 15% at 1:50 dilution and less than 40% at 1:100 dilution are less preferred, the method of the invention also may be practiced with such alkoxylated esters, including those having anti-irritation activity of 10% or more at 1:50 dilution or 20% or more at 1:100 dilution.

The invention also provides compositions containing at least one alkoxylated ester of dicarboxylic or tricarboxylic acid and an irritant. In the preferred embodiment, the compositions of the invention are dilutable, pre-mixed blends containing at least one alkoxylated ester and a surfactant for use in shampoos, body washes, foaming facial cleansers, bubble baths, liquid hand cleaners and other surfactant based applications. In the preferred embodiment, the blends of the invention include 3–20% of the alkoxylated esters of the invention in combination with the surfactants shown in Table 5, as follows:

TABLE 5

| Surfactant | Content (%) |
| --- | --- |
| Anionic surfactant | 0–97 |
| Betaines | 0–97% |
| Amphoteric surfactants | 0–97% |
| Non-ionic surfactants | 0–30% |
| Cationic surfactants | 0–10% |
| Alkanolamides | 0–30% |

One or more surfactant or mixture thereof may be present in the dilutable blend. Sufficient water along with preservatives, fragrance, foam boosters, conditioners, emollients and other cosmetic ingredients can be added to provide finished formulations with reduced irritation in comparison to similar formulations without the alkoxylated esters.

In accordance with another aspect, the invention also provides compositions in the form of various cosmetic and/or personal care products. Such compositions may be referred to as final product compositions, and may be in the form of, for example, sunscreen compositions for hair and/or skin, such as lotions, gels, sprays, and the like, hand cleaners, bath compositions, suntan oils, anti-perspirant compositions, perfumes and colognes, cold creams, pre-shaves, deodorants, topical pharmaceutical ointments, skin moisturizers, facial cleansers, cleansing creams, skin gels, shampoos, hair conditioners, detergents, household cleaning products, make-up products, lipstick products, mascara, and hair coloring products.

The final product compositions of the invention, including preparations for skin and hair, include at least one alkoxylated ester of dicarboxylic or tricarboxylic acid described herein. The amount of the alkoxylated ester(s) having defined anti-irritating properties in the products depend on the specific application, and may vary from about 0.1% to about 40%, more preferably, from about 0.1% to about 10%, yet more preferably, from about 0.5% to about 2% by the weight of the product composition. However, different amounts may be preferred depending on the nature of the product.

The alkoxylated esters of the invention are especially suitable for use in cosmetic and personal care products that are more likely to cause irritation or the use of which makes reduction in irritation especially desirable. The preferred products include shampoos, hair conditioners, sunscreen formulations, baby shampoos, baby bath products, hand dishwashing liquids, body washes, facial washes, non-woven toilettes, baby wipes and bubble bath products. The more preferred products are baby shampoos, baby bath products, hand dishwashing liquids, baby wipes and bubble bath products.

The shampoos containing the alkoxylated esters may include a variety of ingredients, including those traditionally included. Non-limiting examples of such ingredients are Ammonium Lauryl Sulfate, Ammonium Laureth Sulfate, Sodium Lauryl Sulfate, Sodium Laureth Sulfate, Amphoteric Surfactants (e.g., cocoamphoglycinate, cocoamidopropyl betaine and the like), Amine oxides, such as cocoamine oxide and the like, Cellulose and cationic cellulose, for example, Polyquat 10, Guar Gum and Cationic Guar Gum, UV absorbing compounds, such as Benzophenone 3 and Octylmethoxycinnamate, Silicone fluids (Cyclomethicone) modified silicone fluids (Amodimethicone), Botanical extracts, Fatty Esters and triglycerides such as Octyl Stearate and Wheat Germ Oil. Other suitable specific ingredients are described herein in the general ingredients section.

The baby shampoos and baby baths containing the alkoxylated esters may contain a variety of ingredients, including those traditionally included. Non-limiting examples of such ingredients are Ammonium Lauryl Sulfate, Ammonium Laureth Sulfate, Sodium Lauryl Sulfate, Sodium Laureth Sulfate, Amphoteric Surfactants such as cocoamphoglycinate, cocoamidopropyl Betaine and the like, Amine oxides such as cocoamine oxide and the like, Cellulose and cationic cellulose like Polyquat 10, Guar Gum and Cationic Guar Gum, UV absorbing compounds such as Benzophenone 3 and Octylmethoxycinnamate, Silicone fluids (Cyclomethicone) modified silicone fluids (Amodimethicone), Botanical extracts, Fatty Esters and triglycerides such as Octyl Stearate and Wheat Germ Oil, Alkoxylated Glycerides such as PEG-30 Glyceryl Cocoate, Alkoxylated Sorbitan Esters such as Polysorbate 20, Carboxylated surfactants such as Trideceth-10 Carboxylate. Other suitable specific ingredients are described herein in the general ingredients section.

The body and facial washes containing the alkoxylated esters may include a variety of ingredients, including those traditionally included. Non-limiting examples of such ingredients are Ammonium Lauryl Sulfate, Ammonium Laureth Sulfate, Sodium Lauryl Sulfate, Sodium Laureth Sulfate, Amphoteric Surfactants such as cocoamphoglycinate, cocoamidopropyl, Betaines and the like, Amine oxides, such as cocoamine oxide and the like, Cellulose and cationic cellulose like Polyquat 10, Guar Gum and Cationic Guar Gum, UV absorbing compounds such as Benzophenone 3 and Octylmethoxycinnamate, Silicone fluids (Cyclomethicone) modified silicone fluids (Amodimethicone), Botanical extracts, Fatty Esters and triglycerides such as Octyl Stearate and Wheat Germ Oil, Alkoxylated Glycerides such as PEG-30 Glyceryl Cocoate, Alkoxylated Sorbitan Esters such as Polysorbate 20, Carboxylated surfactants such as Trideceth-10 Carboxylate, Lanolin and Lanolin quats, Petrolatum. Other suitable specific ingredients are described herein in the general ingredients section.

The hair conditioners containing the alkoxylated esters may also contain a variety of other ingredients, including those traditionally included. Non-limiting examples of such ingredients are Fatty quats such as Behentrimonium Chloride, Fatty alcohols such as cetyl alcoholCellulose and cationic cellulose like Polyquat 10, Guar Gum and Cationic Guar GumUV absorbing compounds such as Benzophenone 3 and Octylmethoxycinnamate, Silicone fluids (Cyclomethicone) modified silicone fluids (Amodimethicone), Botanical extracts Fatty Esters and triglycerides such as Octyl Stearate and Wheat Germ Oil, Fatty alkyl phosphate esters such as dicetyl phosphate and PEG-20 Cetyl Phosphate. Other suitable specific ingredients are described herein in the general ingredients section.

The hand dish wash liquids containing the alkoxylated esters may also contain a variety of other ingredients, including those traditionally included. Non-limiting examples of such ingredients are Ammonium Lauryl Sulfate, Ammonium Laureth Sulfate, Sodium Lauryl Sulfate, Sodium Laureth Sulfate, Sodium and Magnesium salts of Dodecyl Benzene Sulfonate, Alkanolamides such as Cocamide DEA or Cocoamide MEA, Amphoteric Surfactants such as cocoamphoglycinate, cocoamidopropyl Betaine and the like, Amine oxides such as cocoamine oxide and the like.

The non-woven toilettes and baby wipes containing the alkoxylated esters may also contain a variety of other ingredients, including those traditionally included. Non-limiting examples of such ingredients are Ammonium Lauryl Sulfate, Ammonium Laureth Sulfate, Sodium Lauryl Sulfate, Sodium Laureth Sulfate, Amphoteric Surfactants such as cocoamphoglycinate, cocoamidopropyl Betaine and the like, Amine oxides such as cocoamine oxide and the like, Cellulose and cationic cellulose like Polyquat 10, Guar Gum and Cationic Guar Gum, UV absorbing compounds such as Benzophenone 3 and Octylmethoxycinnamate, Silicone fluids (Cyclomethicone) modified silicone fluids (Amodimethicone), Botanical extracts, Fatty Esters and triglycerides such as Octyl Stearate and Wheat Germ Oil, Alkoxylated Glycerides such as PEG-30 Glyceryl Cocoate, Peg-75 Lanolin, Alkoxylated Sorbitan Esters such as Polysorbate 20, Carboxylated surfactants such as Trideceth-10 Carboxylate, Non-alkoxylated alcohol phosphate esters such as cetyl phosphate or dicetyl phosphate, Alkoxylated alcohol phosphate esters such as PEG-10 Cetyl phosphate and the like. Other suitable specific ingredients are described herein in the general ingredients section.

The bubble bath products containing the alkoxylated esters may also contain a variety of other ingredients, including those traditionally included. Non-limiting examples of such ingredients are Ammonium Lauryl Sulfate, Ammonium Laureth Sulfate, Sodium Lauryl Sulfate, Sodium Laureth Sulfate, Amphoteric Surfactants (e.g., cocoamphoglycinate, cocoamidopropyl betaine and the like), Amine oxides, such as cocoamine oxide and the like, Cellulose and cationic cellulose, for example, Polyquat 10, Guar Gum and Cationic Guar Gum, UV absorbing compounds, such as Benzophenone 3 and Octylmethoxycinnamate, Silicone fluids (Cyclomethicone) modified silicone fluids (Amodimethicone), Botanical extracts, Fatty Esters and triglycerides such as Octyl Stearate and Wheat Germ Oil. Other suitable specific ingredients are described herein in the general ingredients section. Other suitable specific ingredients are described herein in the general ingredients section.

The final product compositions that include the alkoxylated esters may be in the form of liquids, gels, creams, emulsions, foams, and solids; may be clear or opaque; and may be formulated as aqueous and non-aqueous preparations, including but not limited to topical preparations. Therefore, in accordance with another embodiment of the present invention, there is provided a composition for topical application including one or more active ingredients, and fatty alkoxylated ester agents of the present invention.

Aqueous topical preparations in accordance with the present invention include one or more of the alkoxylated esters and one or more active ingredients, with the balance being water. As mentioned above, a separate emollient agent of mineral oil, petrolatum and the like can also be included. However, the compounds of the present invention have emollient properties. Suitable active agents for use in such topical preparations include sunscreens, pigments, moisturizers, film formers, detergents, thickening agents, emulsifiers, antiseptic agents, conditioning agents, and deodorant actives.

The topical preparations of the present invention, in addition to including the compositions of the present invention, one or more active ingredients, water and the optional emollient agent, may also include excipients such as fragrances, proteins, humectants, salts, preservatives, essential oils and the like. These additional components may be added in various amounts as is well-known in the cosmetic formulation art.

Typical aqueous topical preparations in accordance with the present invention include the alkoxylated esters of the present invention, in a range of from about 0.20 to about 40.0 percent by weight of the composition, preferably from about 3.0 to about 20.0 percent by weight of the composition. The one or more active ingredients may be present in an amount from about 0.20 to about 40.0 percent by weight of the composition, preferably from about 3.0 to about 20.0 percent by weight of the composition. When used, the additional emollient is blended with the agents of the present invention in a ratio of about 10:1 to 1:10 parts ester agent of the present invention. The balance is generally excipients and water or some aqueous solvent system.

Non-aqueous topical preparations in accordance with the present invention may also be prepared. Such preparations include the agents of the present invention and one or more of the above-listed active ingredients. An emollient agent of mineral oil, petrolatum, and the like may again optionally be included, as may the above-described excipients fragrances, proteins, humectants, salts, preservatives, essential oils and the like.

Typical non-aqueous topical preparations in accordance with the present invention include the alkoxylated esters of the present invention, in a range of from about 0.20 to about 99.0 percent by weight of the composition, preferably from about 10 to about 90.0 percent by weight of the composition, and more preferably from about 25 to about 75 percent by weight of the composition. The one or more active ingredients may be present in an amount from about 0.20 to about 99.0 percent by weight of the composition, preferably from about 10 to about 90.0 percent by weight of the composition, and more preferably from about 25 to about 75 percent by weight of the composition.

As with the aqueous topical preparations, the emollient agent, when present, may be blended with the agents of the present invention in a ratio of about 10:1 to about 1:10 parts ester agent of the invention.

Preferably, the final product compositions are dispersions or solutions in water, or in a mixture of water with a suitable secondary solvent. Suitable inert solvents include various lower alkanols and glycols. Lower alkanols having from one to four carbon atoms are suitable for use with the present invention, and lower alkanols having from two to three carbon atoms are preferred. Glycols having from three to eight carbon atoms are suitable for use with the present invention, while glycols having from three to six carbon atoms are preferred. Examples of suitable lower alkanols and glycols include methanol, ethanol, isopropanol, butanol, hexylene glycol, 1,3-butylene glycol, 1,2- and 1,3-propane diol, 2-methyl 1,3-propane diol, propylene glycol, diethylene glycol, and the like. The total amount of solvent may be up to about 98% by weight of the composition, preferably, from about 20% to about 90%, more preferably, from about 50% to about 90% by weight of the composition. Again, however, different amounts of solvent may be preferred depending on the nature of the product. If a mixture of water and a secondary solvent is used, the secondary solvent may be present in the amount of up to 90%, preferably, between about 25% and about 80% by weight of water in the composition.

In addition to the alkoxylated esters, the compositions of the invention may include various active and additional ingredients, both conventional and otherwise. Of course, a decision to include an ingredient and the choice of specific active and additional ingredients depends on the specific application and product formulation. Also, the line of demarcation between an "active" ingredient and an "additional ingredient" is artificial and dependent on the specific application and product type. A substance that is an "active" ingredient in one application or product may be an "additional" ingredient in another, and vice versa.

Thus, the compositions of the invention may include one or more active ingredients, which provide some benefit to the object of the application of the composition, for example, hair or skin. Such active ingredients may include one or more substances such as cleaning agents, hair conditioning agents, skin conditioning agents, hair styling agents, antidandruff agents, hair growth promoters, perfumes, sunscreen compounds, pigments, moisturizers, film formers, hair colors, make-up agents, detergents, thickening agents, emulsifiers, antiseptic agents, deodorant actives, surfactants and pharmaceuticals useful for topical purposes for transdermal delivery.

The choice of the active ingredient(s) depends on the nature of the desired cosmetic or personal care product. For example, the sunscreen compounds may be used in the sunscreen lotions, shampoos, medicated shampoos, hair care lotions and the like. For each type of active ingredient, one or more compounds may be present. Likewise, more than one type of active ingredient may be present.

The following ingredients may be present in the compositions of the invention.

Surfactants

Various surfactants may be present in the compositions of the invention, including one or more nonionic surfactants, anionic surfactants, cationic surfactants, amphoteric surfactants, zwitterionic surfactants, and mixtures thereof. For some of surfactants that may be used in combination with the compositions of the invention, please see McCutcheon's, Detergents and Emulsifiers, (1986), U.S. Pat. Nos. 5,151, 210, 5,151,209, 5,120,532, 5,011,681, 4,788,006, 4,741,855, U.S. Pat. Nos. 4,704,272, 4,557,853, 4,421,769, 3,755,560; all incorporated herein by reference in their entirety.

Cationic Surfactants

Alkoxylated esters of the invention are cationic surfactants suitable for use in various personal care products, especially hair care products such as conditioners and shampoos. In addition, other cationic surfactants may be present in the compositions of the invention. The amounts and the nature of cationic surfactants present in the compositions of the invention depend on the nature of the composition. In the final product composition, the total amount of cationic surfactants, including the alkoxylated esters thereof described herein, may vary from 0.1% to about 40%, more preferably, from about 0.1% to about 15%, yet more preferably, from about 0.5% to about 2% by the weight of the product composition. However, different amounts of cationic surfactants may be preferred depending on the nature of the product. Suitable additional cationic surfactants are disclosed in McCutcheon, Detergents & Emulsifiers, (M.C. Publishing Co. 1979); U.S. Pat. Nos. 3,155,591, 3,929,678, 3,959,461, 4,387,090, which are incorporated by reference herein.

Ammonium Quats

The compositions of the invention may include quaternary ammonium cationic surfactants of the formula

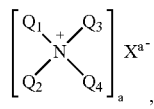

where X and a are as previously described, $Q_1$ is $C_{12}-C_{22}$ alkyl, $C_{12}-C_{22}$ alkyl amido $C_1-C_6$ alkylene, $C_{12}-C_{22}$ alkylhydroxy; $Q_2$ is $C_{12}-C_{22}$ alkyl, $C_{12}-C_{22}$ alkyl amido $C_1-C_6$ alkylene, $C_{12}-C_{22}$ alkylhydroxy, benzyl, or $C_1-C_6$ alkyl; $Q_3$ and $Q_4$ are independently $C_1-C_6$ alkyl or benzyl.

Examples of suitable quaternary ammonium surfactants include cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl dimethyl ammonium chloride, distearyl methyl ammonium bromide, and mixtures thereof.

Additional quaternary ammonium salts include those wherein the $C_{12}-C_{22}$ alkyl is derived from a tallow fatty acid or from a coconut fatty acid. Examples of quaternary ammonium salts derived from these tallow and coconut sources include ditallow dimethyl ammonium chloride, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl) dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

More preferred quaternary ammonium surfactants are dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Fatty Amines

The compositions of the invention may also include salts of primary, secondary and tertiary $C_{12}-C_{22}$ amines. Examples of such suitable amines include stearamido propyl dimethyl amine, diethyl amino ethyl stearamide, dimethyl stearamine, dimethyl soyamine, soyamine, tri(decyl)amine, ethyl stearylamine, ethoxylated stearylamine, dihydroxyethyl stearylamine, and arachidylbehenylamine. Suitable amine salts include the halogen, acetate, phosphate, nitrate, citrate, lactate and alkyl sulfate salts. Such salts include stearylamine hydrochloride, soyamine chloride, stearylamine formate, N-tallowpropane diamine dichloride and stearamidopropyl dimethylamine citrate. Some cationic amine surfactants useful in the compositions of the present invention are disclosed in U.S. Pat. No. 4,275,055, incorporated by reference herein.

Amidoamines

The compositions of the invention may also include aminoamides, such as disclosed in U.S. patent application Ser. No. 09/409,203, assigned to Croda Inc., and incorporated by reference herein.

Non-ionic Surfactants

The compositions of the invention may also include various non-ionic surfactants. Among the suitable nonionic surfactants are condensation products of $C_8-C_{30}$ alcohols with sugar or starch polymers. These compounds can be represented by the formula $(S)_n$—O—R, wherein S is a sugar moiety such as glucose, fructose, mannose, and galactose; n is an integer of from about 1 to about 1000, and R is $C_8-C_{30}$ alkyl. Examples of suitable $C_8-C_{30}$ alcohols from which the R group may be derived include decyl alcohol, cetyl alcohol, stearyl alcohol, lauryl alcohol, myristyl alcohol, oleyl alcohol, and the like. Specific examples of these surfactants include decyl polyglucoside and lauryl polyglucoside.

Other suitable nonionic surfactants include the condensation products of alkylene oxides with fatty acids (i.e., alkylene oxide esters of fatty acids). These materials have the general formula $RCO(X)_n OH$, wherein R is a $C_{10}-C_{30}$ alkyl, X is —$OCH_2CH_2$— (derived from ethylene oxide) or —$OCH_2CHCH_3$— (derived from propylene oxide), and n is an integer from about 1 to about 200.

Yet other suitable nonionic surfactants are the condensation products of alkylene oxides with fatty acids (i.e., alkylene oxide diesters of fatty acids) having the formula RCO(X)$_n$OOCR, wherein R is a C$_{10}$–C$_{30}$ alkyl, X is —OCH$_2$CH$_2$— (derived from ethylene oxide) or —OCH$_2$CHCH$_3$— (derived from propylene oxide), and n is an integer from about 1 to about 200.

Yet other nonionic surfactants are the condensation products of alkylene oxides with fatty alcohols (i.e., alkylene oxide ethers of fatty alcohols) having the general formula R(X)$_n$OR', wherein R is C$_{10}$–C$_{30}$ alkyl, n is an integer from about 1 to about 200, and R' is H or a C$_{10}$–C$_{30}$ alkyl.

Still other nonionic surfactants are the compounds having the formula RCO(X)$_n$OR' wherein R and R' are C$_{10}$–C$_{30}$ alkyl, X is —OCH$_2$CH$_2$— (derived from ethylene oxide) or —OCH$_2$CHCH$_3$— (derived from propylene oxide), and n is an integer from about 1 to about 200.

Examples of alkylene oxide-derived nonionic surfactants include ceteth-1, ceteth-2, ceteth-6, ceteth-10, ceteth-12, ceteraeth-2, ceteareth6, ceteareth-10, ceteareth-12, steareth-1, steareth-2, stearteth-6, steareth-10, steareth-12, PEG-2 stearate, PEG4 stearate, PEG6 stearate, PEG-10 stearate, PEG-12 stearate, PEG-20 glyceryl stearate, PEG-80 glyceryl tallowate, PPG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Still other useful nonionic surfactants include polyhydroxy fatty acid amides disclosed, for example, in U.S. Pat. Nos. 2,965,576, 2,703,798, and 1,985,424, which are incorporated herein by reference.

Anionic Surfactants

The compositions of the invention may also include various anionic surfactants. Several examples of suitable anionic surfactants are disclosed in U.S. Pat. No. 3,929,678, which is incorporated herein by reference. Further examples of suitable anionic surfactants include alkoyl isethionates, and alkyl ether sulfates.

The alkoyl isethionates typically have the formula RCO—OCH$_2$CH$_2$—SO$_3$M, wherein R is C$_{10}$–C$_{30}$ alkyl, and M is a water-soluble cation, such as ammonium, sodium, potassium, or triethanolamine. The examples of suitable isethionates include ammonium cocoyl isethionate, sodium cocoyl isethionate, sodium lauroyl isethionate, sodium stearoyl isethionate, and mixtures thereof. Preferred for used herein are ammonium cocoyl isethionate, sodium cocoyl isethionate, and mixtures thereof.

The alkyl ether sulfates typically have the formulas ROSO$_3$M and RO(C$_2$H$_4$O)$_x$SO$_3$M, where R is C$_{10}$–C$_{30}$ alkyl, x varies from about 1 to about 10, and M is a water-soluble cation such as ammonium, sodium, potassium and triethanolamine.

Yet another suitable class of anionic surfactants are alkali metal salts of C$_8$–C$_{30}$ carboxylic acids and alkylsulfonates of the formula R$_1$—SO$_3$M (where R$_1$ is C$_8$–C$_{30}$ alkyl; preferably, C$_{12}$–C$_{22}$ alkyl, and M is a cation), including succinamates, and C$_{12}$–C$_{24}$ olefin sulfonates and carboxylates.

Amphoteric Surfactants

The compositions of the invention may also include zwitterionic and amphoteric surfactants. Suitable amphoteric and zwitterionic surfactants are, for example, derivatives of mono- or di-C$_8$–C$_{24}$ secondary and tertiary amines, such as alkyl imino acetates, carboxylates, sulfonates, sulfates, phosphates, and phosphonates, including iminodialkanoates and aminoalkanoates of the formulas RN(CH$_2$)$_m$CO$_2$M$_2$ and RNH(CH$_2$)$_m$CO$_2$M, where m varies from 1 to 4, R is C$_8$–C$_{30}$ alkyl; preferably, C$_{12}$–C$_{22}$ alkyl, and M is H, alkali metal, alkaline earth metal ammonium, or alkanolammonium.

Other suitable amphoteric and zwitterionic surfactants are imidazolinium and ammonium derivates. Suitable examples of such amphoteric surfactants include sodium 3-dodecyl-aminopropionate, sodium 3-dodecylaminopropane sulfonate, N-alkyltaurines; N-higher alkyl aspartic acids, and coamidopropyl PG-dimonium chloride phosphate. For further examples of suitable amphoteric and zwitterionic surfactants, please see U.S. Pat. Nos. 2,658,072, 2,438,091, and 2,528,378, which are incorporated herein by reference Yet other suitable amphoteric and zwitterionic surfactants are betaines. Examples of suitable betaines include coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl) alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, and amidobetaines and amidosulfobetaines, oleyl betaine, and cocamidopropyl betaine.

Sunscreen Compounds

A wide variety of sunscreen compounds are suitable for use with the compositions of the present invention. Depending on the nature of the composition, the sunscreen compounds may be added in the amount of up to about 40% by weight of the composition, preferably, from about 1% to about 30%. However, the preferred amount may vary depending on the nature of the composition. Thus, for the final product compositions in the form of a shampoo or conditioner, the suitable sunscreen agent may be included in the amount of up to about 40% by weight of the composition, preferably, from about 0.5% to about 5%, more preferably, from about 05 to about 1.5% by weight of the composition. Suitable sunscreen compounds include, for example, p-aminobenzoic acid, its salts and its derivatives; anthranilates; salicylates; cinnamic acid derivatives; dihydroxycinnamic acid derivatives; trihydroxycinnamic acid derivatives; hydrocarbons; dibenzalacetone and benzalacetophenone; naphtholsulfonates; dihydroxy-naphtholic acid and its salts; coumarin derivatives; diazoles; quinine salts; quinoline derivatives; hydroxy- or methoxy-substituted benzophenones; uric and vilouric acids; tannic acid and its derivatives; hydroquinone; amino benzoates, salicylates, ferrulic acid derivatives, phenylbenzimidazole sulfonic acids, benzophenone sulfonic acids, thioctic acids derivatives, oil-soluble cinnamates, and benzophenones. For other suitable sunscreen compounds, please see Segarin, et al., Cosmetics Science and Technology, Chapter VIII, pages 189 et seq., incorporated herein by reference.

Specific suitable sunscreen compounds include 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl-4->bis(hydroxypropyl)!-aminobenzoate, 2-ethylhexyl-2-cyano-3, 3-diphenylacrylate, 2-ethylhexylsalicylate, glyceryl p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethyl-aminophenyl)-5-sulfonicbenzoxazoic acid, para-aminobenzoic acid, benzophenone-1, benzophenone-1, benzophenone-2, benzophenone-3, benzophenone-4, benzophenone-5, benzophenone-6, benzophenone-8, benzophenone-12, methoxycinnamate, avobenzone, ethyl dihydroxypropyl para-aminobenzoate, glyceryl para-aminobenzoate, methyl anthranilate, octocrylene, octyl dimethyl para-aminobenzoate, octyl methoxycinnamate, octyl salicylate, zinc oxide, titanium dioxide, and red petrolatum.

Emollients

The compositions of the invention may also include one or emollient compounds such as fats, waxes, lipids, silicones, hydrocarbons, fatty alcohols and a wide variety of solvent materials. The amount of the emollient depends on the application. For the final product compositions, emollients are included in the amount of up to 50% by weight of the composition, preferably, from about 0.1% to about 20%, and more preferably, from about 0.5% to about 10% by weight of the composition.

Examples of suitable emollients include $C_{8-30}$ alkyl esters of $C_{8-30}$ carboxylic acids; $C_{1-6}$ diol monoesters and diesters of $C_{8-30}$ carboxylic acids; monoglycerides, diglycerides, and triglycerides of $C_{8-30}$ carboxylic acids, cholesterol esters of $C_{8-30}$ carboxylic acids, cholesterol, and hydrocarbons. Examples of these materials include diisopropyl adipate, isopropyl myristate, isopropyl palmitate, ethylhexyl palmitate, isodecyl neopentanoate, $C_{12-15}$ alcohols benzoates, diethylhexyl maleate, PPG-14 butyl ether, PPG-2 myristyl ether propionate, cetyl ricinoleate, cholesterol stearate, cholesterol isosterate, cholesterol acetate, jojoba oil, cocoa butter, shea butter, lanolin, lanolin esters, mineral oil, petrolatum, and straight and branched $C_{16}$–$C_{30}$ hydrocarbons.

Also useful are straight and branched chain fatty $C_8$–$C_{30}$ alcohols, for example, stearyl alcohol, isostearyl alcohol, ehenyl alcohol, cetyl alcohol, isocetyl alcohol, and mixtures thereof. Examples of other suitable emollients are disclosed in U.S. Pat. No. 4,919,934; which is incorporated herein by reference in its entirety.

Other suitable emollients are various alkoxylated ethers, diethers, esters, diesters, and trimesters. Examples of suitable alkoxylated ethers include PPG-10 butyl ether, PPG-11 butyl ether, PPG-12 butyl ether, PPG-13 butyl ether, PPG-14 butyl ether, PPG-15 butyl ether, PPG-16 butyl ether, PPG-17 butyl ether, PPG-18 butyl ether, PPG-19 butyl ether, PPG-20 butyl ether, PPG-22 butyl ether, PPG-24 butyl ether, PPG-30 butyl ether, PPG-11 stearyl ether, PPG-15 stearyl ether, PPG-10 oleyl ether, PPG-7 lauryl ether, PPG-30 isocetyl ether, PPG-10 glyceryl ether, PPG-15 glyceryl ether, PPG-10 butyleneglycol ether, PPG-15 butylene glycol ether, PPG-27 glyceryl ether, PPG-30 cetyl ether, PPG-28 cetyl ether, PPG-10 cetyl ether, PPG-10 hexylene glycol ether, PPG-15 hexylene glycol ether, PPG-10 1,2,6-hexanetriol ether, PPG-15 1,2,6-hexanetriol ether, and mixtures thereof.

Examples of alkoxylated diethers include PPG-10 1,4-butanediol diether, PPG-12 1,4-butanediol diether, PPG-14 1,4-butanediol diether, PPG-2 butanediol diether, PPG-10 1,6-hexanediol diether, PPG-12 1,6-hexanediol diether, PPG-14 hexanediol diether, PPG-20 hexanediol diether, and mixtures thereof. Preferred are those selected from the group consisting of PPG-10 1,4-butanediol diether, PPG-12 1,4-butanediol diether, PPG-10 1,6-hexandiol diether, and PPG-12 hexanediol diether, and mixtures thereof.

Suitable lipids include $C_8$–$C_{20}$ alcohol monosorbitan esters, $C_8$–$C_{20}$ alcohol sorbitan diesters, $C_8$–$C_{20}$ alcohol sorbitan triesters, $C_8$–$C_{20}$ alcohol sucrose monoesters, $C_8$–$C_{20}$ alcohol sucrose diesters, $C_8$–$C_{20}$ alcohol sucrose triesters, and $C_8$–$C_{20}$ fatty alcohol esters of $C_2$–$C_{62}$-hydroxy acids. Examples of specific suitable lipids are sorbitan diisostearate, sorbitan dioleate, sorbitan distearate, sorbitan isosotearate, sorbitan laurate, sorbitan oleate, sorbitan palmitate, sorbitan sesquioleate, sorbitan esquistearte, sorbitan stearate, sorbitan triiostearate, sorbitan trioleate, orbitan tristeate, sucrose cocoate, sucrodilaurate, sucrose distearate, sucrose laurate, sucrose myristate, sucrose oleate, sucrose palmitate, sucrose ricinoleate, sucrose stearate, sucrose tribehenate, sucrose tristearate, myristyl lactate, stearyl lactate, isostearyl lactate, cetyl lactate, palmityl lactate, cocoyl lactate, and mixtures thereof.

Other suitable emollients include mineral oil, petrolatum, cholesterol, dimethicone, dimethiconol, stearyl alcohol, cetyl alcohol, behenyl alcohol, diisopropyl adipate, isopropyl myristate, myristyl myristate, cetyl ricinoleate, sorbitan distearte, sorbitan dilaurate, sorbitan stearate, sorbitan laurate, sucrose laurate, sucrose dilaurate, sodium isostearyl lactylate, lauryl pidolate, sorbitan stearate, stearyl acohol, cetyl alcohol, behenyl alcohol, PPG-14 butyl ether, PPG-15 stearyl ether, and mixtures thereof.

Emulsifiers

The compositions of the invention may also include various emulsifiers. In the final product compositions of the invention, emulsifiers may be included in the amount of up to about 10%, preferably, in the amount of from about 0.5% to about 5% by weight of the composition. The examples of suitable emulsifiers include stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, polyethyleneglycols, polypropyleneglyocis, and mixtures thereof.

Anti-Dandruff

The compositions of the invention may also include antidandruff agents. The examples of suitable antidandruff agents include zinc pyrithione, sulphur, and selenium sulfide.

Hair Oxidizers

The compositions of the invention may also include hair oxidizing/reducing agents. The examples of suitable hair oxidizing/reducing agents include hydrogen peroxide, perborate, thioglycolates and persulfate salts.

Thickeners

The compositions of the invention may also include various thickeners, such as cross-linked acrylates, nonionic polyacrylamides, xanthan gum, guar gum, gellan gum, and the like; polyalkyl siloxanes, polyaryl siloxanes, and aminosilicones. In the final product compositions of the invention, thickeners may be included in the amount of up to about 10%, preferably, in the amount of from about 0.2% to about 5% by weight of the composition.

The specific examples of the suitable thickening silicon compounds include polydimethylsiloxane, phenylsilicone, polydiethylsiloxane, and polymethylphenylsiloxane. Some of the suitable silicon compounds are described in European Patent Application EP 95,238 and U.S. Pat. No. 4,185,017, which are incorporated herein by reference. The compositions of the invention may also include silicone polymer materials, which provide both style retention and conditioning benefits to the hair. Such materials are described in U.S. Pat. No. 4,902,499, which is incorporated herein by reference.

Hair Conditioning Agents

The compositions of the invention may also include hydrolyzed animal protein hair conditioning agents. Croda Incorporated sells an example of a commercially available material under the tradename Crotein Q-RTM. Other examples include urea, glycerol, and propoxylated glycerols, including those described in U.S. Pat. No. 4,976,953, which is incorporated by reference herein.

Hair Setting Agents

The compositions of the invention may also include a hair setting agent to impart styling benefits upon application to hair. The hair setting polymers may be homopolymers, copolymers, terpolymers, etc. For convenience in describing the polymers hereof, monomeric units present in the polymers may be referred to as the monomers from which they can be derived. The monomers can be ionic (e.g., anionic, cationic, amphoteric, zwitterionic) or nonionic.

Examples of anionic monomers include unsaturated carboxylic acid monomers such as acrylic acid, methacrylic acid, maleic acid, maleic acid half ester, itaconic acid, fumaric acid, and crotonic acid; half esters of an unsaturated polybasic acid anhydride such as succinic anhydride, phthalic anhydride or the like with a hydroxyl group-containing acrylate and/or methacrylate such as hydroxyethyl acrylate and, hydroxyethyl methacrylate, hydroxypropyl acrylate and the like; monomers having a sulfonic acid group such as styrenesulfonic acid, sulfoethyl acrylate and methacrylate, and the like; and monomers having a phosphoric acid group such as acid phosphooxyethyl acrylate and methacrylate, 3-chloro-2-acid phosphooxypropyl acrylate and methacrylate, and the like.

Examples of cationic monomers include monomers derived from acrylic acid or methacrylic acid, and a quaternarized epihalohydrin product of a trialkylamine having 1 to 5 carbon atoms in the alkyl such as (meth)acryloxypropyltrimethylammonium chloride and (meth)acryloxypropyl-triethylammonium bromide; amine derivatives of methacrylic acid or amine derivatives of methacrylamide derived from methacrylic acid or methacrylamide and a dialkylalkanolamine having $C_1$–$C_6$ alkyl groups such as dimethylaminoethyl (meth)acrylate, diethylaminoethyl (meth)acrylate, dimethylaminopropyl (meth)acrylate, or dimethylaminopropyl (meth)acrylamide.

Examples of the amphoteric monomers include zwitterionized derivatives of the aforementioned amine derivatives of (meth)acrylic acids or the amine derivatives of (meth)acrylamide such as dimethylaminoethyl (meth)acrylate, dimethylaminopropyl(meth)acrylamide by a halogenated fatty acid salt such as potassium monochloroacetate, sodium monobromopropionate, aminomethylpropanol salt of monochloroacetic acid, triethanolamine salts of monochloroacetic acid and the like; and amine derivatives of (meth) acrylic acid or (meth)acrylamide, as discussed above, modified with propanesultone.

Examples of nonionic monomers are acrylic or methacrylic acid esters of $C_1$–$C_{24}$ alcohols, such as methanol, ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol, cyclohexanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, 1-dodecanol, 1-hexadecanol, 1-octadecanol, styrene; chlorostyrene; vinyl esters such as vinyl acetate; vinyl chloride; vinylidene chloride; acrylonitrile; alpha-methylstyrene; t-butylstyrene; butadiene; cyclohexadiene; ethylene; propylene; vinyl toluene; alkoxyalkyl (meth)acrylate, methoxy ethyl (meth)acrylate, butoxyethyl (meth)acrylate; allyl acrylate, allyl methacrylate, cyclohexyl acrylate and methacrylate, oleyl acrylate and methacrylate, benzyl acrylate and methacrylate, tetrahydrofurfuryl acrylate and methacrylate, ethylene glycol di-acrylate and -methacrylate, 1,3-butyleneglycol di-acrylate and -methacrylate, diacetonacrylamide, isobornyl (meth)acrylate, n-butyl methacrylate, isobutyl methacrylate, 2-ethylhexyl methacrylate, methyl methacrylate, t-butylacrylate, t-butylmethacrylate, and mixtures thereof.

Examples of anionic hair styling polymers are copolymers of vinyl acetate and crotonic acid, terpolymers of vinyl acetate, crotonic acid and a vinyl ester of an alpha-branched saturated aliphatic monocarboxylic acid such as vinyl neodecanoate; and copolymers of methyl vinyl ether and maleic anhydride, acrylic copolymers and terpolymers containing acrylic acid or methacrylic acid.

Examples of cationic hair styling polymers are copolymers of amino-functional acrylate monomers such as lower alkylamino alkyl acrylate or methacrylate monomers such as dimethyl aminoethylmethacrylate with compatible monomers such as N-vinylpyrrolidone or alkyl methacrylates such as methyl methacrylate and ethyl methacrylate and alkyl acrylates such as methyl acrylate and butyl acrylate.

Miscellaneous Components

The compositions of the invention may also include a wide range of miscellaneous ingredients. Some suitable miscellaneous ingredients commonly used in the cosmetic and personal care industry are described in The CTFA Cosmetic Ingredient Handbook, ($2^{nd}$ Ed., 1992), which is incorporated by reference herein.

Thus, the compositions of the invention may also include one or more absorbents, anti-acne agents, anti-perspirants, anticaking agents, antifoaming agents, antimicrobial agents, antioxidants, antidandruff agents, astringents, binders, buffers, biological additives, buffering agents, bulking agents, chelating agents, chemical additives, coupling agents, conditioners, colorants, cosmetic astringents, cosmetic biocides, denaturants, drug astringents, detergents, dispersants, external analgesics, film formers, foaming agents, fragrance components, humectants, keratolytics, opacifying agents, pH adjusters, preservatives, propellants, proteins, retinoids, reducing agents, sequestrants, skin bleaching agents, skin-conditioning agents (humectants, miscellaneous, and occulsive), skin soothing agents, skin healing agents, softeners, solubilizing agents, lubricants, penetrants, plastisizers, solvents and co-solvents, sunscreening additives, salts, essential oils, and vitamins.

The examples of suitable pH adjusters include sodium hydroxide, triethanoleamine, and aminomethylpropanol, and mixtures thereof. If pH adjusters are present in a final product composition, the amount may vary from about 0.01% to about 5%, preferably, from about 0.1% to about 2% by weight of the composition.

The examples of suitable film formers include glycerin/diethylene glycol myrystate copolymer, glycerin/diethylene glycol adipate copolymer, ethyl ester of PVM/MA copolymer, PVP/dimethiconylacrylate/polycarbamyl/polyglycol ester, and mixtures thereof. If the film formers are present in the final product compositions, the amount may vary from about 0.1% to about 15.0% by weight of the composition, preferably, from about 0.1% to about 2.5% by weight of the composition.

The examples of suitable vitamins include tocopherol, tocopherol acetate, retinoic acid, retinol, and retinoids.

The examples of suitable anti-acne medicaments include resorcinol, sulfur, salicylic acid, erythromycin, zinc, and benzoyl peroxide.

The examples of suitable skin bleaching or lightening agents include hydroquinone, and kojic acid. The examples of suitable aesthetic components such as fragrances, pigments, colorings, and the like, include panthenol and derivatives (e.g., ethyl panthenol), aloe vera, pantothenic acid and its derivatives, clove oil, menthol, camphor, eucalyptus oil, eugenol, menthyl lactate, witch hazel distillate, allantoin, bisabolol, and dipotassium glycyrrhizinate.

The compositions of the invention are further illustrated in the examples that follow.

EXAMPLE 1

Preparation of PPG-3-PEG-4 Cetyl Ether 2351 g (9.7 moles) of cetyl alcohol was placed in a dry stirred pressure vessel fitted with a nitrogen inlet. The cetyl alcohol was heated until molten, and 5.75 g of NaOH was added, with stirring, as a 40% aqueous solution. The vessel was purged with nitrogen and further heated to 110° C. Vacuum was applied for 1 hour to remove the water vapors from the headspace of the vessel, and the mixture was further heated to 155° C. After 1690 g of propylene oxide and 1709 g of ethylene oxide were mixed and added, the reaction mixture was stirred for additional 1.5 hours to complete the reaction. The progress of the reaction was monitored by the uptake of the reagent and the measurement of the pressure in the vessel. The reaction mixture was cooled to 110° C., and a vacuum was applied for approximately 1 hour. To neutralize NaOH in the reaction mixture, 42 g of 25% sulfuric acid was added. The mixture is stirred for 10 minutes, and the pH was adjusted to 7. Upon cooling, PEG-4-PPG-3 cetyl ether, a viscous liquid, was isolated as the major product.

EXAMPLE 2

Preparation of Di-PPG-3-PEG-4 Cetyl Ether Adipate

A four-necked flask, fitted with a mechanical stirrer, a thermometer and a nitrogen inlet was charged with 1778 g (2.96 moles) of PPG-3-PEG-4 cetyl ether, a 221 g (1.52 moles) of adipic acid and 1.5 g of SnO. The mixture was heated to 220° C. The progress of the reaction was monitored by measuring the acid values of the reaction mixture over time. Once the acid value was stable, the mixture was cooled to 22° C. 4 g of 30% aqueous solution of $H_2O_2$ and 70 g of water were added, and the mixture was heated again to 75° C. The water was evaporated under vacuum, producing di-PPG-3-PEG-4 as the major product.

EXAMPLE 3

Evaluation for Anti-Irritancy with 3% of Alkoxylated Ester in a Shampoo Base

Anti-irritation activity of Di-PPG-2-PEG-10 Myristyl Ether Adipate and Di-PPG-3-PEG-4 Cetyl Ether Adipate was evaluated by using a proprietary shampoo base, at the concentration of the evaluated alkoxylated ester of 3%. The shampoo base contained all usual ingredients of a typical shampoo with the exception of a nonionic surfactant and a thickener. The evaluation of the anti-irritation activity was carried out by using the above-described TEP assay test methodology. Table 6 shows the content of the test compositions A1 (Di-PPG-2-PEG-10 Myristyl Ether Adipate) and B1 (Di-PPG-3-PEG-4 Cetyl Ether Adipate) and the control composition C1:

TABLE 6

|  | A1 | B1 | — | C1 |
|---|---|---|---|---|
| Shampoo Base | 96% | 96% |  | 99% |
| Crothix Liquid* | 1% | 1% |  | 1% |
| Di-PPG-2-PEG-10 Myristyl Ether Adipate | 3% | — |  | — |
| Di-PPG-3-PEG-4 Cetyl Ether Adipate | — | 3% |  | — |

*PEG-150 Pentaerthrityl Tetrastearate (and) PEG-6 Caprylic/Capric Glycerides (and) Water.

Table 7 shows the percentages of intracellular leakage of sodium fluorescein for compositions A1, B1, and C1:

TABLE 7

| Composition | Percentage Leakage at 1:50 Dilution | Percentage Leakage at 1:50 Dilution |
|---|---|---|
| A1 | 48% | 15% |
| B1 | 36% | 6% |
| C1 | 64% | 47% |

As seen from Table 7, both Di-PPG-2-PEG-10 Myristyl Ether Adipate and Di-PPG-3-PEG-4 Cetyl Ether Adipate show anti-irritating activity, with the magnitude of activity being substantially greater for Di-PPG-3-PEG-4 Cetyl Ether Adipate (test composition B1).

EXAMPLE 4

Evaluation for Anti-Irritancy in Reference to a Market Baby Shampoo

A market-available sample of J&J Baby Shampoo (Lot #1199NB) was purchased in a store. Test composition A2 was prepared by adding alkoxylated ester to the J&J Baby Shampoo, which was also used as a control. It is a common practice to use J&J's Baby Shampoo as a control in in vitro experiments involving surfactant systems in the cosmetic industry. Table 8 compares test composition A2 and a commercial sample of J&J Baby Shampoo:

TABLE 8

|  | Percentage Leakage at 1:50 Dilution | Percentage Leakage at 1:100 Dilution |
|---|---|---|
| Test Composition A2 | 48% | 15% |
| Market Baby Shampoo | 60% | 39% |

It is evident from this comparison that composition A2 containing alkoxylated ester is capable of generating anti-irritation effects comparable or superior to other raw materials sold into this market.

EXAMPLE 5

Evaluation of Anti-irritation Activity of di-PPG-3-PEG-4 Myristyl Ether Adipate in Reference to Market Baby Shampoo Test composition A3 was prepared by adding di-PPG-3-PEG-4 Myristyl Ether Adipate to J&J Baby Shampoo (to a content of 5% of the ester and 95% of the shampoo). The shampoo without the ester was used as a control. The irritation potentials of the test composition A3 and the control were measured by the TEP assay as described. The results of the measurements are shown in Table 9 (as intracellular leakage of sodium fluorescein):

TABLE 9

|  | Percentage Leakage at 1:50 Dilution | Percentage Leakage at 1:100 Dilution |
|---|---|---|
| Test Composition A3 | 14.2% | 17.4% |
| Market Baby Shampoo | 64.5% | 44.8% |

As seen in Table 9, di-PPG-3-PEG-4 Myristyl Ether Adipate causes a dramatic reduction in the irritation potential of the shampoo, indicating substantial anti-irritation activity.

EXAMPLE 6

Synthetic Liquid Soap

| Ingredients | % |
|---|---|
| PART A | |
| CRODASINIC LS-30 (Sodium Lauroyl Sarcosinate) | 7.0 |
| INCROMIDE CA (Cocamide DEA) | 5.0 |
| Sodium Laureth Sulfate | 18.0 |
| Di-PPG-2 Steareth-10 Adipate | 3.0 |
| GLYCEROX HE (PEG-7 Glyceryl Cocoate) | 2.5 |
| SUPER SOLAN (PEG-75 Lanolin) | 2.5 |
| Sodium Chloride | 1.0 |
| Deionized Water | 58.5 |
| Ethylene Glycol Monostearate | 1.5 |
| PART B | |
| Propylene Glycol (and) Methyl Paraben (and) Propyl Paraben (and) Diazolidinyl Urea) (1) | 1.0 |
| Lactic Acid to pH 7.00 | |

Procedure: Combine ingredients with mixing and heat to 75–80° C. Cool to 40° C. Add Part B. Cool to desired fill temperature. Adjust pH with Lactic Acid if necessary.

EXAMPLE 7

Clear Body Wash

| Ingredients | % |
|---|---|
| PART A | |
| Deionized Water | 51.9 |
| SLES (3 mole) | 20.0 |
| Di-PPG-2 Steareth-10 Adipate | 3.0 |
| CROSULTAINE C-50 (Cocamidopropyl Hydroxysultaine) | 12.0 |
| Disodium EDTA | 0.1 |
| PART B | |
| INCROMIDE CA (Cocamide DEA) | 3.0 |
| GLYCEROX 767 (PEG-6 Capric/Caprylic Triglycerides) | 3.0 |
| CROTHIX LIQUID (PEG-150 Pentaerythrityl Tetrastearate (and) PEG-6 Caprylic/Capric Glycerides (and) water) | 3.0 |
| PART C | |
| CROTEIN C-50 (Hydrolyzed Collagen) | 1.0 |
| INCROMECTANT LAMEA (Acetamide MEA (and) (Lactamide MEA) | 1.0 |
| 10% Citric Acid Solution | 1.0 |
| Propylene Glycol (and) Diazolidinyl Urea (and) Methyl Paraben (and) Propyl Paraben (1) | 1.0 |
| pH = 5.0 + 0.5 | |
| Viscosity = 5,500 + 10% (RVT Spindle #3, 10 rpm, 25° C.) 1) | |

Procedure: Combine ingredients of Part A with mixing. Combine ingredients of Part B with mixing and heat to 50° C. Slowly add Part B to Part A with mixing. Add ingredients of Part C to Part A individually with mixing. Mix until uniform.

EXAMPLE 8

Mild Diswashing Liquid

| Ingredient | Supplier | Weight Percent |
|---|---|---|
| Water | — | 60 |
| Calsoft L-40 | Pilot Chemical | 18.0 |
| Calfoam ES-303 | Pilot Chemical | 12.0 |
| INCROMIDE OXIDE C | Croda | 5.0 |
| Di-PPG-2 Steareth-10 Adipate | Croda | 3.0 |
| Sodium chloride | Various | 1–2 |
| Dye, fragrance, preservative | Various | q.s. |

EXAMPLE 9

Silky Bubble Bath

| Ingredients | % |
|---|---|
| PHASE A | |
| INCROSUL OTS (Disodium Oleth-3 Sulfosuccinate) | 35.00 |
| INCROMINE OXIDE C (Cocamidopropylamine Oxide) | 3.50 |
| INCROMIDE LR (Lauramide DEA) | 2.00 |
| CROVOL PK-70 (PEG-45 Palm Kernel Glycerides) | 5.00 |
| Di-PPG-2 Steareth-10 Adipate | 3.00 |
| Sodium Chloride | 1.25 |
| Deionized Water | 45.75 |
| PHASE B | |
| CRODAPEARL LIQUID (Sodium Laureth Sulfate (and) Hydroxyethyl Stearamide MIPA) | 3.00 |
| CROSILK LIQUID (Silk Amino Acids) | .50 |
| Germaben II (1) | 1.00 |
| Citric to pH 6.0 | |

Procedure: Combine Phase A with slight heating to 65° C. When clear, stop heating, continue mixing, and cool to 45° C. At 45° C. add Phase B. Continue cooling and mixing to room temperature and adjust the pH next.

EXAMPLE 10

Baby Shampoo

| Ingredients | % |
|---|---|
| Part A | |
| SLES (3 mole) | 20.0 |
| CROSULTAINE C-50 (Cocamidopropyl Hydroxysultaine) | 12.0 |
| Deionized Water | 45.5 |
| Part B | |
| CROVOL A-70 (PEG-60 Almond Glycerides) | 15.0 |
| Di-PPG-2 Steareth-10 Adipate | 3.0 |
| CROTHIX LIQUID (PEG-150 Pentaerythrityl Tetrastearate and PEG-6 Caprylic/Capric Glycerides (and) water) | 3.5 |
| PART C | |
| Propylene Glycol (and) Diazolidinyl Urea (and) Methyl Paraben (and) Propyl Paraben (1) | 1.0 |

Procedure: combine the ingredients of part A with mixing. Combine the ingredients of part B with mixing and heat to 50° C. Add part B to part A with mixing. Add the ingredients of part C individually with mixing. Adjust pH if needed with a 10% HCl aqueous solution. Cool with mixing to desired fill temperature.

PH=6.22+0.5; viscosity: 9,200CPS+10% (RVT SPINDLE #4, 10 RPM, @ 25° C.)

EXAMPLE 11

Sunscreen Lotion

A sunscreen lotion includes the following ingredients:

| Phase A | |
|---|---|
| Ingredient (s) | % W/W |
| Di-erucic imidazoline quat | 1.0 |
| Benzophenone 3 | 6.0 |
| Cetearyl Alcohol | 4.0 |
| Di-PPG-3-PEG-4 Steareth Adipate | 5.0 |
| Octyl Methoxycinnamate | 7.5 |

| Phase B | |
|---|---|
| Ingredient | W/W % |
| Water | 65.50 |

| Phase C | |
|---|---|
| Ingredient | W/W % |
| Germaben II (preservative) | 1.0 |

The sunscreen lotion is prepared as follows. The ingredients of Phase A are combined and heated to 75° C. In a separate vessel, the ingredients of Phase B are also combined and heated to 75° C. Phase A is added to Phase B with stirring, and the stirring is continued while the combined phases are cooled to 40° C. Phase C is added, the cooling is continued to 25° C., providing the desired lotion.

EXAMPLE 12

Sunscreen Spray Lotion

A sunscreen spray lotion includes the following ingredients:

| Ingredient | % W/W |
|---|---|
| Phase A | |
| Dibehenyldimethyl ammonium chloride | 1.0 |
| Di-PPG-3 Myristyl Ether Adipate | 11.0 |
| Benzophenone 3 | 6.0 |
| Octyl Methoxycinnamate | 7.0 |
| Menthyl Anthranilate | 5.0 |
| Di-PPG-2 Steareth-10 Adipate | 3.0 |
| Phase B | |
| Water | 66 |
| Sodium Hydroxide | 0.1 |
| Phase C | |
| Germaben II (preservative) | 1.0 |

The sunscreen spray lotion is prepared as follows. The ingredients of Phase A are combined and heated to 75° C. In a separate vessel, the ingredients of Phase B are also combined and heated to 75° C. Phase A is added to Phase B with stirring, and the stirring is continued while the combined phases are cooled to 40° C. Phase C is added, the cooling is continued to 25° C., providing the desired lotion.

EXAMPLE 13

Hair Conditioner

A hair conditioner includes the following ingredients:

| Ingredient | % W/W |
|---|---|
| Phase A | |
| Di-C$_{20-24}$ Immidazoline Quat | 1.0 |
| Cromollient SCE (Di-PPG-2 Steareth-10 Adipate) | 5.0 |
| Cetyl Alcohol | 4.0 |
| Phase B | |
| Water | 89 |
| Phase C | |
| Germaben II (preservative) | 1.0 |

The hair conditioner is prepared as follows. The ingredients of Phase A are combined and heated to 75° C. In a separate vessel, the ingredients of Phase B are also combined and heated to 75° C. Phase A is added to Phase B with stirring, and the stirring is continued while the combined phases are cooled to 40° C. Phase C is added, the cooling is continued to 25° C., providing the desired lotion.

EXAMPLE 14

Conditioning Shampoo

A conditioning shampoo includes the following ingredients:

| Ingredient | % W/W |
|---|---|
| Phase A | |
| Ammonium Lauryl Sulfate | 25.0 |
| Ammonium Laureth Sulfate | 12.0 |
| Crosultaine C-50 (Cocamidopropyl Hydroxysultaine) | 3.0 |
| Lauramide DEA | 1.0 |
| Cromollient DCA34 (Di-PPG-3 Myreth-4 Adipate) | 4.0 |
| Germaben II (Preservative) | 1.0 |
| Phase B | |
| Di-Erucic Imidazoline Quat | 2.0 |

The conditioning shampoo is prepared as follows. The ingredients of phase A are combined and heated to 60° C. Phase B is added to the combined phase A and with continued stirring while allowing the mixture to cool to 25° C.

Unless stated to the contrary, any use of the words such as "including," "containing," "comprising," "having" and the like, means "including without limitation" and shall not be construed to limit any general statement that it follows to the specific or similar items or matters immediately following it. Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

Although the invention herein has been described with reference to particular embodiments, it is to be understood that these embodiments are merely illustrative of the principles and applications of the present invention. It is therefore understood that numerous modifications may be made to the illustrative embodiments and that other arrangements may be devised without departing from the spirit and scope of the present invention as described by the appended claims.

The invention claimed is:

1. An alkoxylated ester of a dicarboxylic acid having an anti-irritating activity, measured as a reduction in intracellular leakage of sodium fluorescein, of 15% or more at 1:50 dilution or 40% or more at 1:100 dilution from a test composition containing 5% of said alkoxylated ester;

and having the formula (I):

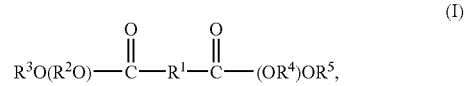

where —COR$^1$CO— is a dicarboxylic group of an aliphatic dicarboxylic acid and R$^1$ is an alkyl group, saturated or unsaturated, straight chain or branched, cyclic or acyclic, having 0 to 20 carbon atoms, or —COR$^1$CO— is a dicarboxylic group of an aromatic dicarboxylic acid and R$^1$ is an aromatic nucleus of the aromatic dicarboxylic acid, having 6 to 20 carbon atoms;

R$^2$O— and R$^4$O—, which may be the same or different, are alkoxylated moieties of the formula

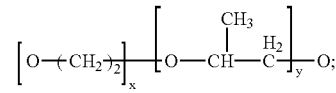

x ranges from 0 to 200 and y ranges from 0 to 200;

R$^3$ and R$^5$, which may be the same or different, are independently alkyl, alkylaryl, or arylalkyl groups, straight chain or branched, saturated or unsaturated, having, containing from 6 to 30 carbon atoms, or hydrogen with the proviso that not more than one of R$^3$ and R$^5$ can be hydrogen;

and further wherein R$^3$ and R$^5$ have 16 to 22 carbon atoms, or x/y ranges from 1 to 2.5, or the weight percentage of the ethoxy groups in the groups (R$^2$O) and (R$^4$O) with respect to the molecular weight of the groups R$^3$O(R$^2$O)— and R$^5$O(R$^4$O)—, respectively, is over 20%.

2. The alkoxylated ester of a tricarboxylic acid having an anti-irritating activity, measured as a reduction in intracellular leakage of sodium fluorescein, of 15% or more at 1:50 dilution or 40% or more at 1:100 dilution from a test composition containing 5% of said alkoxylated ester;

and having the formula:

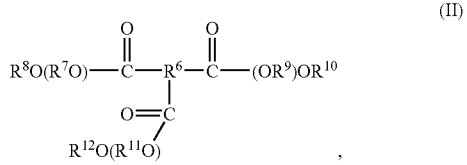

where —COR$^6$CO— is a tricarboxylic group of aliphatic tricarboxylic acid and R$^6$ is an alkyl group, saturated or unsaturated, straight chain or branched, cyclic or acyclic, having 1 to 19 carbon atoms, or —COR$^6$CO— is a tricarboxylic group of aromatic tricarboxylic acid, and R$^6$ is an aromatic nucleus of the aromatic tricarboxylic acid having 6 to 20 carbon atoms;

R$^7$O—, R$^9$O, and R$^{11}$O—, which may be same or different, are alkoxylated moieties of the formula $$\left[O-(CH_2)_2\right]_x \left[O-CH(CH_3)-CH_2\right]_y O;$$

x ranges from 0 to 200 and y ranges from 0 to 200;

$R^8$, $R^{10}$, and $R^{12}$ are each independently alkyl, alkylaryl, or arylalkyl groups, straight chain or branched, saturated or unsaturated, having from 6 to 30 carbon atoms, or hydrogen with the proviso that not more than one of $R^8$, $R^{10}$, and $R^{12}$ can be hydrogen.

3. The alkoxylated ester of claim 2, wherein —$COR^6CO$— is a tricarboxylic group of aliphatic tricarboxylic acid and $R^6$ has 1 to 6 carbon atoms.

4. The alkoxylated ester of claim 2, wherein $R^6$ is the aromatic nucleus having 6 or 10 carbon atoms.

5. The alkoxylated ester of claim 2, wherein $R^6$ is selected from the group consisting of aryl, phenylaryl, alkylaryl, and naphthalene.

6. The alkoxylated ester of claim 2, wherein $R^8$, $R^{10}$ or $R^{12}$ is hydrogen.

7. The alkoxylated ester of claim 2, wherein the weight percentage of the ethoxy groups in the groups ($R^7O$), ($R^9O$), and ($R^{11}O$) with respect to the molecular weight of the groups $R^8O(R^7O)$—, $R^{10}O(R^9O)$—, and $R^{12}O(R^{11}O)$—, respectively, is over 20%.

8. The alkoxylated ester of claim 2, wherein the weight percentage of the ethoxy groups in the groups ($R^7O$), ($R^9O$), and ($R^{11}O$) with respect to the molecular weight of the groups $R^8O(R^7O)$—, $R^{10}O(R^9O)$—, and $R^{12}O(R^{11}O)$—, respectively, is from 20 to 80%.

9. The alkoxylated ester of claim 2, wherein the weight percentage of the ethoxy groups in the groups ($R^7O$), ($R^9O$), and ($R^{11}O$) with respect to the molecular weight of the groups $R^8O(R^7O)$—, $R^{10}O(R^9O)$—, and $R^{12}O(R^{11}O)$—, respectively, is from 24 to 35%.

10. The alkoxylated ester of claim 2, wherein $R^8$, $R^{10}$, and $R^{12}$ have 6 to 22 carbon atoms.

11. The alkoxylated ester of claim 2, wherein $R^8$, $R^{10}$ and $R^{12}$ have 12 to 22 carbon atoms.

12. The alkoxylated ester of claim 2, wherein $R^8$, $R^{10}$, and $R^{12}$ have 16 to 22 carbon atoms.

13. The alkoxylated ester of claim 2, wherein $R^8$, $R^{10}$, and $R^{12}$ have 18 to 22 carbon atoms.

14. The alkoxylated ester of claim 2, wherein x/y is 2 or greater, and x>y.

15. The alkoxylated ester of claims 2 or 1, wherein x ranges from 1 to 100 and y ranges from 0 to 100.

16. The alkoxylated ester of claims 2 or 1, wherein x ranges from 1 to 40 and y ranges from 0 to 40.

17. The alkoxylated ester of claims 2 or 1, wherein x ranges from 2 to 20 and y ranges from 1 to 5.

18. The alkoxylated ester of claims 2 or 1, wherein x ranges from 3 to 10 and y ranges from 1 to 10.

19. A method of reducing irritation to a human or animal subject from a personal care or cosmetic product comprising:

applying said personal care or cosmetic product to said human or animal subject, wherein said personal care or cosmetic product includes an irritant and at least one alkoxylated ester of dicarboxylic acid of formula (I):

$$R^3O(R^2O)-\overset{O}{\underset{\|}{C}}-R^1-\overset{O}{\underset{\|}{C}}-(OR^4)OR^5, \quad (I)$$

where —$COR^1CO$— is a dicarboxylic group of an aliphatic dicarboxylic acid and $R^1$ is an alkyl group, saturated or unsaturated, straight chain or branched, cyclic or acyclic, having 0 to 20 carbon atoms, or —$COR^1CO$— is a dicarboxylic group of an aromatic dicarboxylic acid and $R^1$ is an aromatic nucleus of the aromatic dicarboxylic acid, having 6 to 20 carbon atoms;

$R^2O$— and $R^4O$—, which may be the same or different, are alkoxylated moieties of the formula $$\left[O-(CH_2)_2\right]_x \left[O-CH(CH_3)-CH_2\right]_y O;$$

x ranges from 0 to 200 and y ranges from 0 to 200;

$R^3$ and $R^5$, which may be the same or different, are independently alkyl, alkylaryl, or arylalkyl groups, straight chain or branched, saturated or unsaturated, having, containing from 6 to 30 carbon atoms, or hydrogen with the proviso that not more than one of $R^3$ and $R^5$ can be hydrogen;

and further wherein $R^3$ and $R^5$ have 16 to 22 carbon atoms, or x/y ranges from 1 to 2.5, or the weight percentage of the ethoxy groups in the groups ($R^2O$) and ($R^4O$) with respect to the molecular weight of the groups $R^3O(R^2O)$— and $R^5O(R^4O)$—, respectively, is over 20%;

or tricarboxylic acid of formula (II), $$R^8O(R^7O)-\overset{O}{\underset{\|}{C}}-\underset{\underset{O=C}{\underset{|}{R^6}}}{R^6}-\overset{O}{\underset{\|}{C}}-(OR^9)OR^{10} \quad (II)$$
$$\phantom{xxxxxxxxx} | \phantom{xx} R^{12}O(R^{11}O)$$

where $COR^6CO$— is a tricarboxylic group of aliphatic tricarboxylic acid and $R^6$ is an alkyl group, saturated or unsaturated, straight chain or branched, cyclic or acyclic, having 1 to 19 carbon atoms, or —$COR^6CO$— is a tricarboxylic group of aromatic tricarboxylic acid, and $R^6$ is an aromatic nucleus of the aromatic tricarboxylic acid having 6 to 20 carbon atoms;

$R^7O$—, $R^9O$, and $R^{11}O$—, which may be same or different, are alkoxylated moieties of the formula $$\left[O-(CH_2)_2\right]_x \left[O-CH(CH_3)-CH_2\right]_y O;$$

x ranges from 0 to 200 and y ranges from 0 to 200;

$R^8$, $R^{10}$, and $R^{12}$ are each independently alkyl, alkylaryl, or arylalkyl groups, straight chain or branched, saturated or unsaturated, having, containing from 6 to 30 carbon atoms, or hydrogen with the proviso that not more than one of $R^8$, $R^{10}$, and $R^{12}$ can be hydrogen;

said alkoxylated ester having anti-irritating activity measured as a reduction in intracellular leakage of sodium fluorescein of 15% or more at 1:50 dilution, or 40% or more at 1:100 dilution, from a test composition containing 5% of the alkoxylated ester.

20. The method of claim 19, wherein said anti-irritating activity is 20% or more at 1:50 dilution or 50% or more at 1:100 dilution.

21. The method of claim 20, wherein said anti-irritating activity is 40% or more at 1:50 dilution or 75% or more at 1:100 dilution.

22. The method of claim 19, wherein said applying step comprises topical application to skin.

23. The method of claim 19, wherein said applying step comprises topical application to hair.

24. The method of claim 19, wherein said irritant is a surfactant.

25. The method of claim 23, wherein said surfactant is selected from the group consisting of non-ionic surfactants, anionic surfactants, cationic surfactants and amphoteric surfactants.

26. The method of claim 19, wherein said personal care or cosmetic product is a shampoo, hair conditioner, sunscreen formulation, baby shampoo, baby bath product, hand dishwashing liquid, body wash, facial wash, non-woven toilette, baby wipe or bubble bath product.

27. The method of claim 19, wherein said at least one alkoxylated ester is the ester of claims 2 or 1.

28. The method of claim 19, wherein said alkoxylated ester is di-PPG-3-PEG-4 Myristyl ether Adipate.

29. The method of claim 19, wherein said alkoxylated ester is di-PPG-2-PEG-10 Steareth Ether Adipate.

30. The method of claim 19, wherein said alkoxylated ester is di-PPG-3-PEG-4 Steareth Ether Adipate.

31. A composition comprising an irritant and at least one alkoxylated ester of claims 2 or 1.

32. The composition of claim 31, wherein said irritant is a surfactant.

33. The composition of claim 32, wherein said surfactant and alkoxylated ester are formed into a pre-mixed blend.

34. The composition of claim 33, further comprising water.

35. The composition of claim 34, wherein said alkoxylated ester is present in the amount from 3 to 20% by weight of the blend.

36. The composition of claim 35, wherein said surfactant is a betaine surfactant present in the amount of from 0 to 97% by weight relative to the total weight of the blend.

37. The composition of claim 35, wherein said surfactant is an amphoteric surfactant present in the amount of from 0 to 97% by weight relative to the total weight of the blend.

38. The composition of claim 35, wherein said surfactant is a non-ionic surfactant present in the amount of from 0 to 30% by weight relative to the total weight of the blend.

39. The composition of claim 35, wherein said surfactant is a cationic surfactant present in the amount of from 0 to 30% by weight relative to the total weight of the blend.

40. The composition of claim 35, wherein said surfactant is alkanolamide present in the amount of from 0 to 30% by weight relative to the total weight of the blend.

41. The composition of claim 35, further comprising a preservative, fragrance, foam booster, conditioner or emollient.

42. The composition of claim 33, wherein said alkoxylated ester is di-PPG-3-PEG-4 Myristyl ether Adipate.

43. The composition of claim 33, wherein said alkoxylated ester is di-PPG-2-PEG-10 Steareth Ether Adipate.

44. The composition of claim 33, wherein said alkoxylated ester is di-PPG-3-PEG-4 Steareth Ether Adipate.

45. The composition of claim 31, wherein said irritant and said alkoxylated ester are included in a cosmetic or personal care product selected from the group consisting of shampoo, hair conditioner, sunscreen formulation, baby shampoo, baby bath product, hand dishwashing liquid, body wash, facial wash, non-woven toilette, baby wipe and bubble bath product.

46. The composition of claim 32, wherein said alkoxylated ester is present in the amount of between about 0.20 and about 40.0 percent by weight relative to the total weight of the composition, further comprising between about 0.20 and about 40.0 percent by weight of an active ingredient relative to the total weight of the composition.

47. The composition of claim 46, wherein said active ingredient is a sunscreen, pigment, moisturizer, film former, detergent, thickening agent, emulsifier, antiseptic agent, conditioner or deodorant.

48. The composition of claim 32, wherein said alkoxylated ester is di-PPG-3-PEG-4 Myristyl ether Adipate.

49. The composition of claim 32, wherein said alkoxylated ester is di-PPG-2-PEG-10 Steareth Ether Adipate.

50. The composition of claim 32, wherein said alkoxylated ester is di-PPG-3-PEG-4 Steareth Ether Adipate.

51. The composition of claim 46, which is an aqueous topical composition.

52. The composition of claim 46, which is a non-aqueous topical composition.

53. The alkoxylated ester of claim 1, wherein —COR$^1$CO— is the dicarboxylic group of aliphatic dicarboxylic acid and $R^1$ has 0 to 6 carbon atoms.

54. The alkoxylated ester of claim 1, wherein $R^1$ is the aromatic nucleus having 6 or 10 carbon atoms.

55. The alkoxylated ester of claim 1, wherein $R^1$ is selected from aryl, phenylaryl, alkylaryl, and naphthalene.

56. The alkoxylated ester of claim 1, wherein $R^3$ and $R^5$ have from 6 to 22 carbon atoms.

57. The alkoxylated ester of claim 1, wherein $R^3$ and $R^5$ have from 12 to 22 carbon atoms.

58. The alkoxylated ester of claim 1, wherein $R^3$ and $R^5$ have 16 to 22 carbon atoms.

59. The alkoxylated ester of claim 1, wherein $R^3$ and $R^5$ have 18 to 22 carbon atoms.

60. The alkoxylated ester of claim 1, wherein x/y ranges from 1 to 2.

61. The alkoxylated ester of claim 1, wherein the weight percentage of the ethoxy groups in the groups ($R^2$O) and ($R^4$O) with respect to the molecular weight of the groups $R^3$O($R^2$O)— and $R^5$O($R^4$O)—, respectively, ranges from 20 to 80%.

62. The alkoxylated ester of claim 1, wherein the weight percentage of the ethoxy groups in the groups ($R^2$O) and ($R^4$O) with respect to the molecular weight of the groups $R^3$O($R^2$O)— and $R^5$O($R^4$O)—, respectively, ranges from 24 to 35%.

63. The alkoxylated ester of claim 2 or 1 having said anti-irritation activity of 40% or more at 1:50 dilution or 75% or more at 1:100 dilution.

64. The alkoxylated ester of claim 2 or 1 having said anti-irritation activity of 20% or more at 1:50 dilution or 50% or more at 1:100 dilution.

65. The alkoxylated ester of claim 2, wherein said $R_8$, $R_{10}$, and $R_{12}$ independently is a lauryl, myristyl, cetyl, stearyl, isostearyl, oleyl or behenyl group.

66. The alkoxylated ester of claim 1, wherein each said $R_3$ and $R_5$ independently is a lauryl, myristyl, cetyl, stearyl, isostearyl, oleyl or behenyl group.

67. The alkoxylated ester of claim 2 or 1, which is PEG-4-PPG-3 steareth ether adipate.

68. The alkoxylated ester of claim 2 or 1, which is PEG-2-PPG-10 steareth ether adipate.

69. The alkoxylated ester of claim 2 or 1, which is PEG-4-PPG-3 myristyl ether adipate.

70. The alkoxylated ester of claim 1, wherein said alkoxylated ester is di-PPG-2-PEG-10 cetyl ether adipate.

71. The composition of claim 32, wherein said alkoxylated ester is 15 di-PPG-2-PEG-10 cetyl ether adipate.

72. The composition of claim 33, wherein said alkoxylated ester is 15 di-PPG-2-PEG-10 cetyl ether adipate.

\* \* \* \* \*

UNITED STATES PATENT AND TRADEMARK OFFICE
CERTIFICATE OF CORRECTION

PATENT NO. : 7,091,243 B2 Page 1 of 1
APPLICATION NO. : 10/215832
DATED : August 15, 2006
INVENTOR(S) : Abel G. Pereira, Laurie B. Joseph and Robert Comber It is certified that error appears in the above-identified patent and that said Letters Patent is hereby corrected as shown below:

On the face of the patent, (75), delete "Cranbury" and insert therefor
--Monroe Township--.
Column 34, line 31, delete ", containing".
Column 36, line 29, delete ", containing".
Column 37, line 3, delete ",containing".
Column 37, line 25, delete "23", and insert therefor --24--/
Column 39, line 1, "claim" should read --claims--.
Column 39, line 4, "claim" should read --claims--.
Column 39, line 13, "claim" should read --claims--.
Column 40, line 1, "claim" should read --claims--.
Column 40, line 3, "claim" should read --claims--.

Signed and Sealed this

Sixth Day of March, 2007

JON W. DUDAS
*Director of the United States Patent and Trademark Office*